US008627731B2

(12) United States Patent
Maheshwari et al.

(10) Patent No.: US 8,627,731 B2
(45) Date of Patent: Jan. 14, 2014

(54) AUTOMATED CASCADE IMPACTOR

(75) Inventors: Krishna Maheshwari, Waltham, MA (US); Rajesh Maheshwari, Milburn, NJ (US)

(73) Assignee: Lab Automate Technologies Inc., Milburn, NJ (US)

( * ) Notice: Subject to any disclaimer, the term of this patent is extended or adjusted under 35 U.S.C. 154(b) by 226 days.

(21) Appl. No.: 13/200,378

(22) Filed: Sep. 23, 2011

(65) Prior Publication Data

US 2012/0247233 A1 Oct. 4, 2012

Related U.S. Application Data

(63) Continuation-in-part of application No. 12/929,051, filed on Dec. 27, 2010, which is a continuation of application No. 12/247,546, filed as application No. PCT/US2007/008924 on Apr. 10, 2007, now Pat. No. 7,926,367.

(60) Provisional application No. 60/744,663, filed on Apr. 11, 2006.

(51) Int. Cl.
*G01N 1/22* (2006.01)

(52) U.S. Cl.
USPC .......... 73/863.22

(58) Field of Classification Search
USPC .......... 73/863.22; 209/138
See application file for complete search history.

(56) References Cited

U.S. PATENT DOCUMENTS

| | | | | |
|---|---|---|---|---|
| 6,453,758 | B1 | 9/2002 | Marple et al. | 73/863.22 |
| 6,723,568 | B1 | 4/2004 | Liu et al. | 436/174 |
| 7,669,488 | B2 | 3/2010 | Bridge et al. | 73/863.22 |
| 2005/0266415 | A1 | 12/2005 | Ryan | 435/6.19 |

FOREIGN PATENT DOCUMENTS

| | | |
|---|---|---|
| EP | 1471344 | 10/2004 |

*Primary Examiner* — Leonard Chang
*Assistant Examiner* — Tamiko Bellamy
(74) *Attorney, Agent, or Firm* — Law Offices of Steven W. Weinrieb

(57) ABSTRACT

An automated cascade impactor is disclosed and comprises a vertical array of a plurality of impactor stages, and a vertical array of isolation stages, wherein the vertical array of the isolation stages comprises pairs of isolation stages between which impactor plates, removed from respective ones of the impactor stages are effectively sandwiched between each pair of isolation stages. Still further, each compactor stage is likewise sandwiched between and upper and a lower pair of the isolation stages.

18 Claims, 14 Drawing Sheets

AUTOMATED CASCADE IMPACTOR

CROSS-REFERENCE TO RELATED PATENT APPLICATIONS

This patent application is a Continuation-in-Part of U.S. patent application Ser. No. 12/929,051, which was filed on Dec. 27, 2010, which is entitled AUTOMATED CASCADE IMPACTOR, and which is a continuation patent application of U.S. patent application Ser. No. 12/247,546 which was filed on Oct. 8, 2008, which is entitled AUTOMATED CASCADE IMPACTOR, which is now U.S. Pat. No. 7,926,367, and which is based upon International Patent Application Serial Number PCT/US2007/008924 which was filed on Apr. 10, 2007, which is entitled AUTOMATED CASCADE IMPACTOR, and which is based upon U.S. Provisional Patent Application Ser. No. 60/744,663 which was filed on Apr. 11, 2006 and which is entitled AUTOMATED CASCADE IMPACTOR.

FIELD OF THE INVENTION

The present invention relates generally to an automated cascade impactor, and more particularly to an automated cascade impactor which comprises a plurality of impactor stages disposed within a vertically oriented array, and a plurality of isolation stages which are also disposed within a vertically oriented array. All of the impactor stages are operatively connected to each other by means of linkage mechanisms which are vertically movable along a vertically oriented extension guide, and an extension actuator is operatively connected to the lowermost one of the impactor stages so as to cause all of the impactor stages to be serially moved to separated states or to compressed states with respect to each other. An isolation actuator is operatively connected to each one of the plurality of isolation stages so as to move all of the isolation stages in a horizontal mode into and out from spaces respectively defined between the plurality of impactor stages when the impactor stages are disposed in their separated states such that the isolation stages can respectively isolate the impactor stages with respect to each other when the impactor stages are moved to their compressed states. In particular, each isolation stage actually comprises a pair of isolation stages which are adapted to be interposed between each impactor stage. A gripper mechanism assembly, comprising pair of vertically stacked gripper arms, is utilized such the impactor plate of each impactor stage is removed from its impactor stage and placed between the pair of isolation stages.

BACKGROUND OF THE INVENTION

Cascade impactors are utilized to determine the aerodynamic particle size distribution and mass concentration levels of solid particulates and liquid aerosols from aerosolized dry powder and aerosolized liquid drug samples that are injected into the cascade impactor. Cascade impactors are also used by the environmental control and monitoring industry in order to determine particulate distributions derived from air samples. One reason for using cascade impactors in a testing environment is that the air flowing through a cascade impactor simulates the air flowing through the human lung. When delivering drugs through the respiratory tract and into the human lung, whether the drug is in the form of microionized powders or in the form of micron-sized droplets of an aerosolized mist from a solution, it is important to know the particle size distribution of the drug.

Only drug particles having a size generally less than five microns in diameter can penetrate deep into the lungs and bronchi. Larger particles will be ingested and then excreted from the body. The deep lung tissue provides an enormous amount of surface area for the active drug substance to get absorbed into the blood-stream and thus permits the efficacious use of lower drug doses to obtain the same or better physiological responses than is capable from drug deliveries by oral means. The measurement of the particle size distribution from the injection of the drug into the cascade impactor is called a dose determination. Dose determination data from a cascade impactor is an integral part of a submission to the FDA as part of an NDA or New Drug Application. Thousands of dose determinations need to be done in order to meet the FDA's submission criteria for a new inhalation drug, and subsequent to the drug approval, thousands of tests are also needed, to be performed over the lifetime of the inhalation drug, as an ongoing quality control measure, in order to continuously demonstrate to the FDA that the performance of the inhalation drug continues to meet the approval criteria or standards for the drug.

While numerous conventional cascade impactors are known and in commercial use, probably the most popular or most commonly used cascade impactor is the Anderson cascade impactor. However, obtaining a dose determination from an Anderson cascade impactor is very labor intensive, error prone, time-consuming, and thus, a very expensive process. For example, or more particularly, conventional procedures for obtaining particle size distribution data using conventional cascade impactors involves very low throughput results since conventional impactors require manual set-up procedures, operations, testing, and dose determination. There are many component parts that need to be carefully disassembled and washed during the use of a conventional cascade impactor in order to obtain a dose determination. Samples must be manually and very carefully collected from the various impactor components, and those components must then be manually assembled in preparation for conducting another dose determination. In addition, the manual process is very prone or susceptible to significant degrees of operator-induced variabilities impacting the generated data. Each operator, that is, lab technician, analyst, or the like, washes or cleans the various components of the cascade impactor in different ways or modes thus causing inconsistencies in the amounts of the drug collected from each impactor stage and from each impactor plate. This inconsistent human washing or cleaning of the plurality of impactor surfaces of the plurality of impactor stages further affects the recovery of the particular drug from the same apparatus for subsequent dose determinations. These operator-induced variabilities can precipitate the need for additional dose determinations to be performed which therefore cause delays in connection with the submission of the dose determination data by the drug companies to the FDA, and therefore, obviously result in delays in the approval of the particular drugs by the FDA. Such delays, of course, can cause the loss of millions of dollars in lost revenue to the drug companies.

Continuing still further, it is to be appreciated that a conventional Anderson cascade impactor comprises a plurality of impactor stages consisting of a plurality of fluid jets or orifices formed within the impactor stages. The particular number of impactor stages or impactor plates used to make up a column of the Anderson cascade impactor is variable and may depend upon the particular drug and the particle size ranges to be measured. The impactor stages are disposed within a vertically stacked array with succeeding impactor stages comprising smaller orifice diameters. Within each impactor stage, there is provided an impactor plate. During a dosing operation, as the drug, suspended within an aerosol stream, is delivered into the throat of the impactor and is subsequently conducted into the impactor stages, the aerosol stream impacts the impactor plate. During a dosing operation, as the drug, suspended within an aerosol stream, is delivered into the throat of the impactor and is subsequently conducted into the impactor stages, the aerosol stream impacts the first one of the impactor plates. Based upon the particle velocity and mass, particles with higher momentum adhere to the first impactor plate. Particles with insufficient momentum bounce up from the first impactor plate so as to go through the succeeding impactor stage disposed beneath the first impactor plate. Each impactor stage is provided with a multitude of orifices of the same diameter, however, succeeding impactor stages are provided with orifices of progressively smaller diameters. Accordingly, as the particles travel through succeeding impactor stages, they gain velocity and hence momentum and settle upon successive impactor plates. Thus, particles of different size ranges or diameters are collected mostly upon the impactor plates while other or remaining particles within the aerosol stream collect upon the impactor stages, thereby inherently providing the impactor with the desired or requisite separation capabilities of the particles within the aerosol stream by means of particle size.

Accordingly, the automated cascade impactor system, as disclosed within the aforenoted U.S. Pat. No. 7,926,367, and the aforenoted U.S. patent application Ser. No. 12/929,051, was developed so as to effectively overcome the various previously noted operational drawbacks characteristic of the aforenoted conventional manually operated cascade impactors. However, while the aforenoted automated cascade impactor has effectively revolutionized dose determination technology and the industry that performs dose determinations in support of, for example, NDAs presented to the FDA for approval, further improvements were deemed necessary or desired. For example, it was desired to improve the collection efficiency of the drug. In addition, it was desired to implement a system wherein the amount of solvent used was capable of being significantly reduced. Still further, it was desired to implement a system wherein the drug could be collected separately from impactor plates of the impactor stages in addition to, or in lieu of, collection of the drug from the impactor stages per se.

A need therefore exists in the art for a new and improved automated cascade impactor wherein the collection efficiency of the drug could be improved, wherein the amount of solvent used was capable of being significantly reduced, and wherein the drug could be collected separately from the impactor plates of the impactor stages in addition to, or in lieu of, collection of the drug from the impactor stages per se.

SUMMARY OF THE INVENTION

The foregoing and other objectives are achieved in accordance with the teachings and principles of the present invention through the provision of a new and improved automated cascade impactor which comprises a vertical array of a plurality of impactor stages, and a vertical array of isolation stages, wherein the vertical array of the isolation stages comprises pairs of isolation stages between which impactor plates, removed from respective ones of the impactor stages are effectively sandwiched between each pair of isolation stages. Still further, each compactor stage is likewise sandwiched between and upper and a lower pair of the isolation stages.

BRIEF DESCRIPTION OF THE DRAWINGS

Various other features and attendant advantages of the present invention will be more fully appreciated from the following detailed description when considered in connection with the accompanying drawings in which like reference characters designate like or corresponding parts throughout the several views, and wherein.

DETAILED DESCRIPTION OF THE ILLUSTRATED EMBODIMENTS

Figure 1:
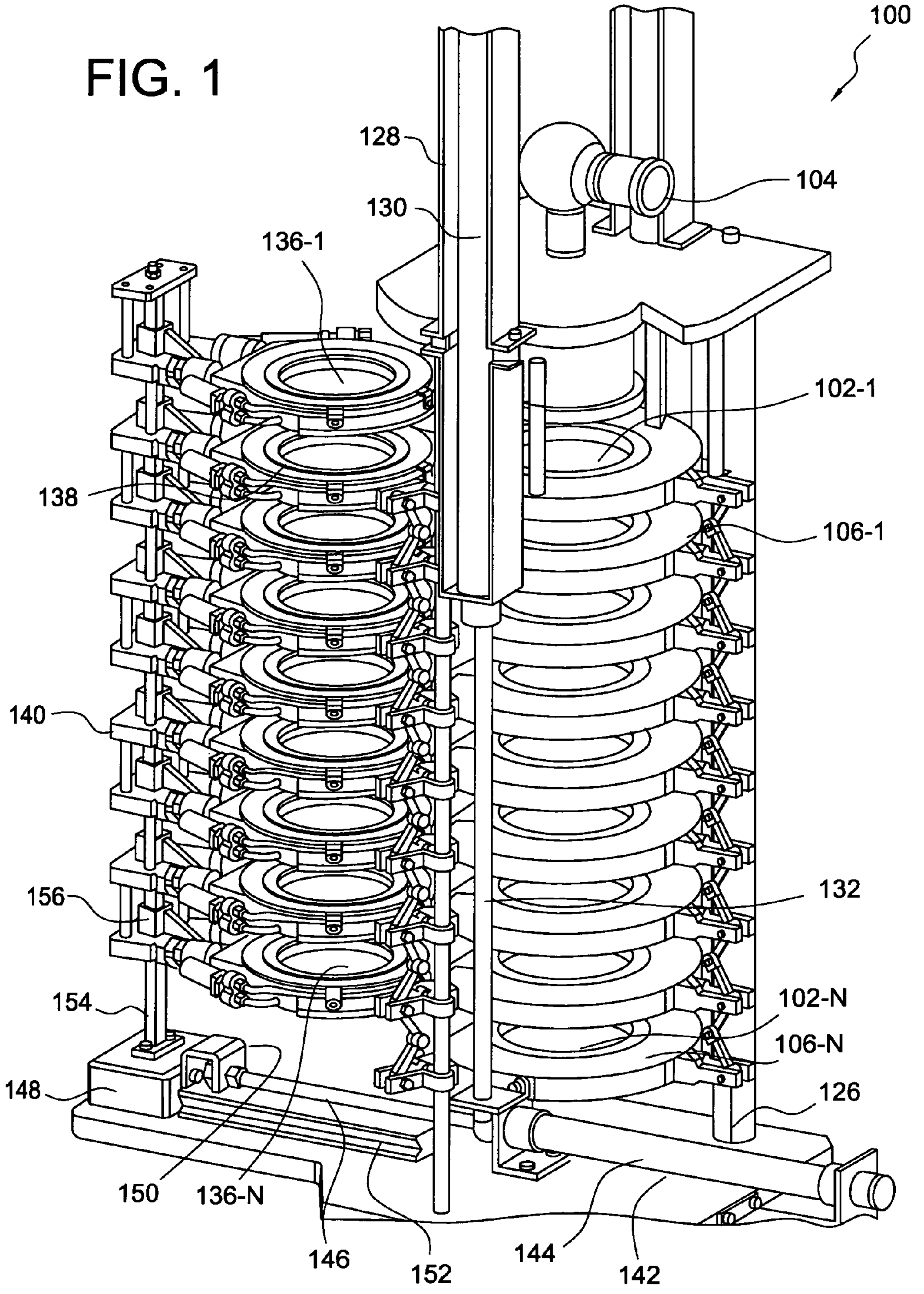
FIG. 1 is a perspective view of an automated cascade impactor previously developed by one of the inventors of the present invention, and upon which the present invention further improves automated cascade impactors.

Referring now to the drawings, and initially, more particularly to FIGS. 1-8 thereof, while a full and complete disclosure of the basic automated cascade impactor may be found within the aforenoted U.S. Pat. No. 7,926,367, and the aforenoted U.S. patent application Ser. No. 12/929,051, which patent and patent application are hereby incorporated by reference, a brief description of the basic automated cascade impactor will first be provided for continuity purposes with respect to the ensuing detailed description of the present invention forming the basis for this continuation-in-part (CIP) patent application. More particularly, the basic automated cascade impactor is generally indicated by the reference character 100 and, as has been noted, is used to conduct dose determinations. The basic automated cascade impactor 100 is seen to comprise a vertically oriented stacked array of a plurality of impactor stages 102-1 through 102-N, and an entry throat 104 is operatively connected to the uppermost one of the plurality of impactor stages 102-1 so as to effectively couple a delivery device, such as, for example, an inhaler or the like, to the plurality of impactor stages 102-N whereby the dispensing of particulate matter, such as, for example, drug particulates within an aerosol spray, into the plurality of impactor stages 102-N can be achieved. Each one of the plurality of impactor stages 102-N is disposed within an encircling frame member or housing 106, as can best be appreciated from FIG. 6, and a pair of mounting brackets 108,110 are fixedly attached to external peripheral portions of each one of the frame members or housings 106 so as to effectively form a clevis member. Lower end portions of a pair of linkage members 112,114 are respectively pivotally mounted within the mounting brackets 108,110 of a lower one of two vertically adjacent frame members or housings 106 of the impactor stages 102-N, by means of a transversely oriented pivot pin 116, so as to extend upwardly toward the upper one of the two vertically adjacent frame members 106, while the upper end portion of a single linkage member 118 is pivotally mounted within the mounting brackets 108,110 of the upper one of the two vertically adjacent frame members of housings 106 of the impactor stages 102-N, by means of a transversely oriented pivot pin 120, so as to extend downwardly toward the lower one of the two vertically adjacent frame members 106. The lower end portion of the single linkage member 118 is pivotally connected to upper end portions of the pair of linkage members 112,114, by means of a transversely oriented pivot pin 122, and in this manner, adjacent frame members or housings 106, within which are respectively disposed the impactor stages 102-N, are operatively connected together.

Continuing further, it is additionally seen that each one of the mounting brackets 110 is provided with a collar or sleeve member 124, and that each collar or sleeve member 124 is slidably mounted upon at least one vertically oriented extension guide 126. An impactor stage extension actuator 128, which may comprise, for example, a piston-cylinder assembly comprising a cylinder mechanism 130 and an extensible/retractible piston rod 132, has the lower end portion of the piston rod 132 fixedly connected to the frame member or housing 106 of the lowermost one 102-N of the plurality of impactor stages 102-1 through 102-N by means of a suitable mounting bracket 134, as can best be seen in FIGS. 2-5, and in this manner, when the piston rod 132 is moved to its extended state, as shown, for example, within FIG. 1, the plurality of impactor stages 102-1 through 102-N are disposed in their separated states, while when the piston rod 132 is moved to its retracted state as shown, for example, within FIG. 2, the plurality of impactor stages 102-1 through 102-N are disposed in their compressed states.

It is to be appreciated that when the lowermost impactor stage 102-N is moved upwardly as a result of the retraction of the piston rod 132 with respect to the cylinder 130 of the extension actuator 128, all of the impactor stages disposed above the lowermost impactor stage 102-N will effectively be forced to move upwardly as respectively guided by means of the collar or sleeve members 124 sliding along the at least one vertically oriented extension guide 126, whereas, conversely, when the lowermost impactor stage 102-N is moved downwardly as a result of the extension of the piston rod 132 with respect to the cylinder 130 of the extension actuator 128, all of the impactor stages disposed above the lowermost impactor stage 102-N will move downwardly as respectively guided by means of the collar or sleeve members 124 sliding along the at least one vertically oriented extension guide 126 and as the link-age connections 112,114, 118, interposed between adjacent or successive ones of the plurality of impactor stages 102-N, permit.

With reference again being made to FIGS. 1-5, it is also seen that the basic automated cascade impactor 100 comprises a vertically oriented stacked array of a plurality of isolation stages 136-1 through 136-N. Each one of the plurality of isolation stages 136-N is disposed within an encircling frame member or housing 138, as can best be appreciated from FIG. 7, and it is additionally seen that each one of the isolation stage encircling frame members or housings 138 is substantially fixedly connected to a mounting plate 140. An isolation actuator 142, which may comprise, for example, a piston-cylinder assembly comprising a cylinder mechanism 144 and an extensible/retractible piston rod 146, has the distal end portion of the piston rod 146 fixedly connected to a support block 148 by means of a suitable inverted U-shaped mounting bracket 150, and it is appreciated further that the mounting block 148 is slidably disposed upon a guide rail 152. A vertically oriented isolation armature 154 has its lower end portion fixedly mounted upon the mounting block 148, and, as can best be appreciated from FIGS. 1 and 8, each one of the isolation stage mounting plates 140 is provided with an upstanding collar or sleeve member 156 which is adapted to be slidably disposed upon the vertically oriented armature 154 so as to permit each one of the isolation stages 136-N to move vertically upwardly and downwardly along the isolation armature 154. Accordingly, it can be further appreciated that when the plurality of impactor stages 102-N are disposed in their separated states, as disclosed within FIGS. 1,3, and 4, the plurality of isolation stages 136-N may be moved in a horizontal mode to positions respectively interposed between the plurality of impactor stages 102-N, as a result of the retraction of the piston rod 146 of the isolation actuator 142, which causes the mounting block 148 to move toward the right along the guide rail 152, and to also cause the isolation armature 154 to move toward the right, as disclosed within FIG. 4, thereby in fact respectively interposing the plurality of isolation stages 136-N between the plurality of impactor stages 102-N.

Figure 2:
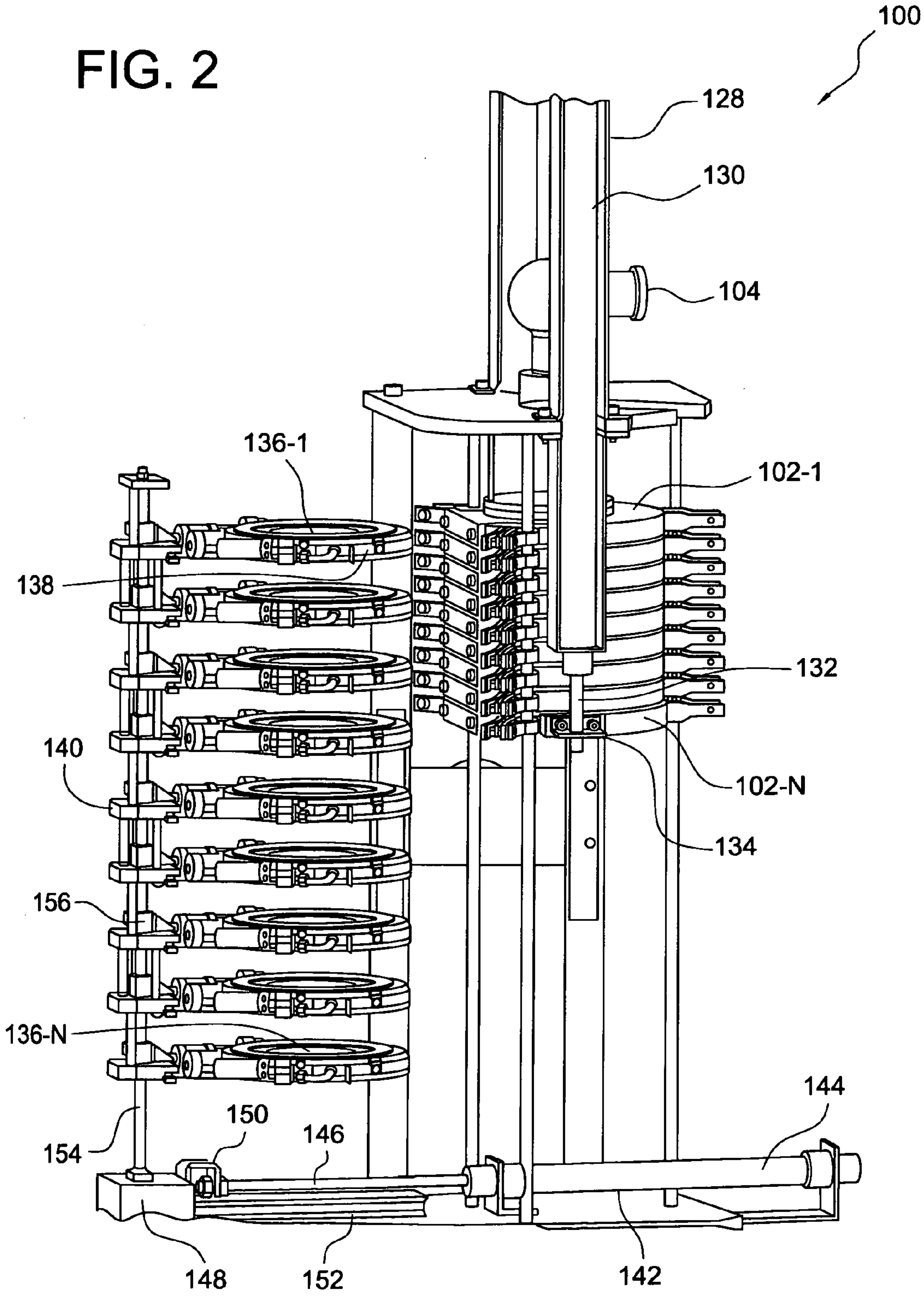
FIG. 2 is a substantially side elevational view of the automated cascade impactor as shown in FIG. 1 illustrating, however, the plurality of impactor stages when the impactor stages are disposed in their compressed states with respect to each other.

Initially, the plurality of impact stages 102-N are moved to their compressed states, as illustrated within FIG. 2, such that the plurality of impactor stages 102-N are effectively disposed in the proper configuration with respect to each other at which the administration of a dose regimen can be implemented as a result of operatively connecting an inhaler device or similar delivery system to the entry throat 104. After the administration of the drug particles to each one of the plurality of impactor stages 102-N has been completed, that is, once the plurality of impactor stages 102-N have collected the drug samples, the extension actuator 128 can be activated such that the piston rod 132 thereof is moved to its extended position, as a result of which the plurality of impactor stages 102-N are moved to their decompressed or separated states whereby spaces will automatically be formed between adjacent impactor stages 102-N. Accordingly, upon activation of the isolation actuator 142, and more particularly, the retraction of the piston rod 146, the isolation armature 154 automatically moves the plurality of isolation stages 136-N into the spaces defined between successive or adjacent ones of the plurality of impactor stages 102-N such that the plurality of isolation stages 136-N are now respectively interposed between successive or adjacent pairs of the impactor stages 102-N as illustrated within FIG. 4.

Figure 4:
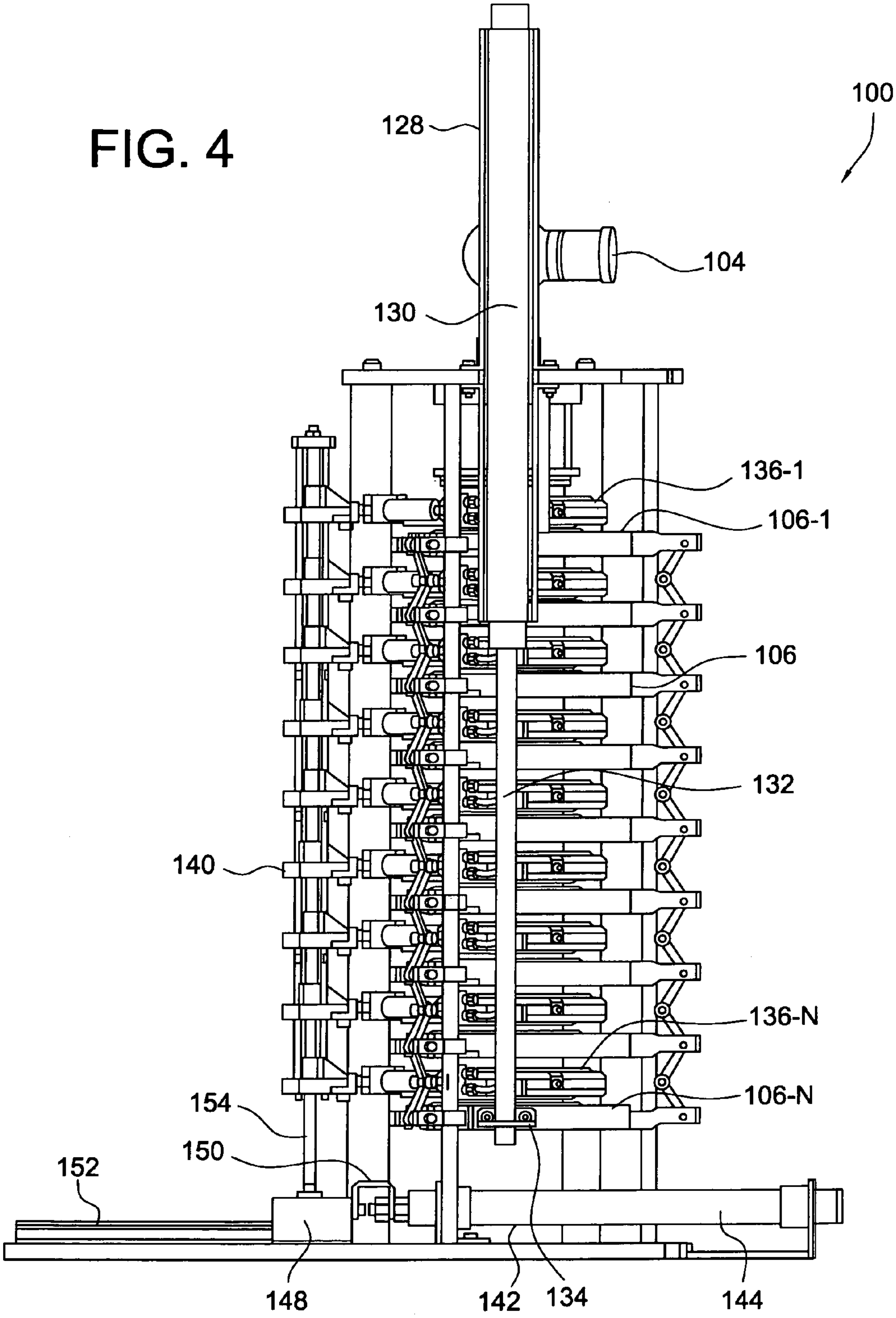
FIG. 4 is a substantially side elevational view of the automated cascade impactor as shown in FIG. 3 illustrating, however, the state in which the plurality of isolation stages have been moved into the spaces defined between adjacent pairs of the impactor stages when the impactor stages are disposed in their separated states with respect to each other.
Figure 5:
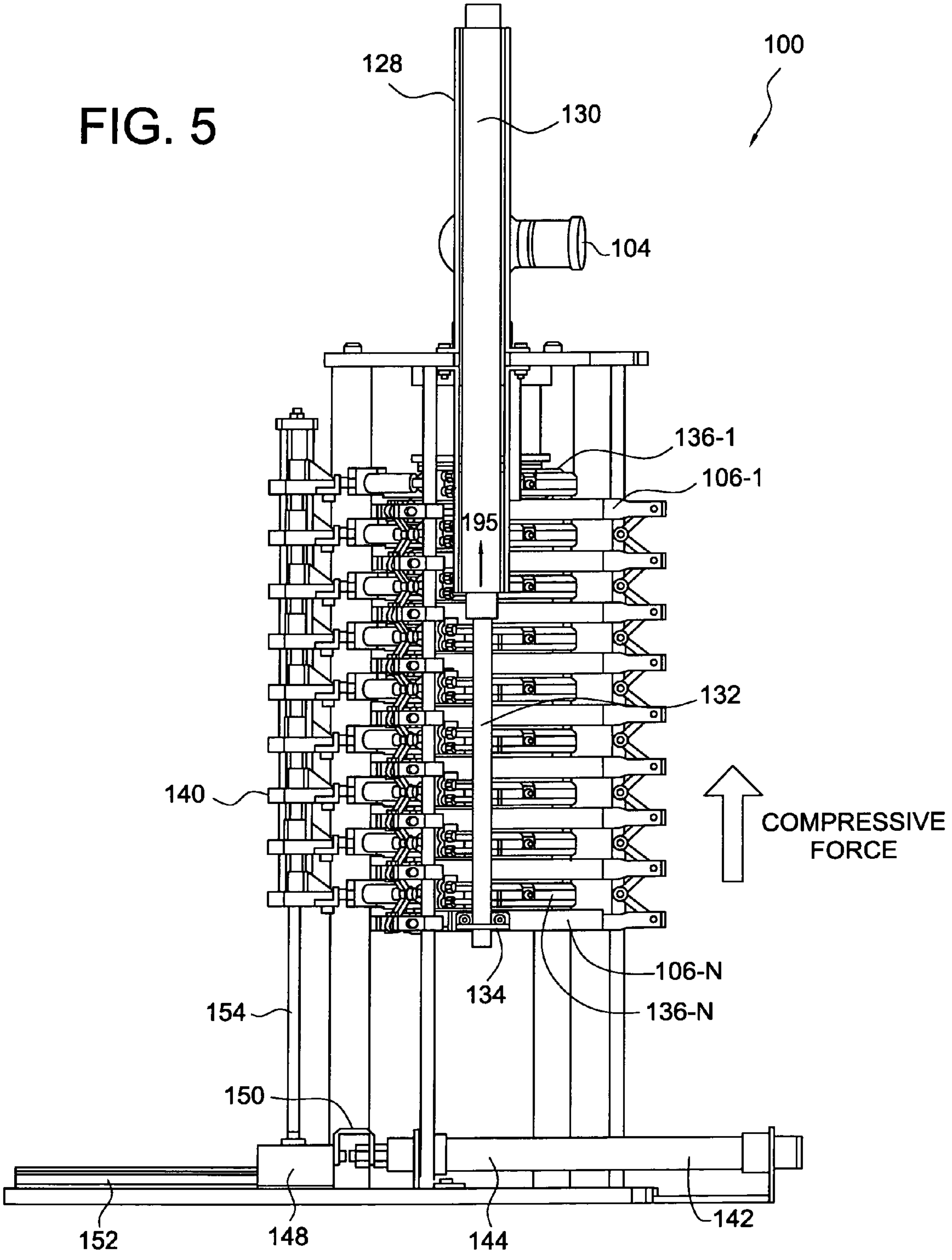
FIG. 5 is a substantially side elevational view of the automated cascade impactor as shown in FIG. 4 illustrating, however, the disposition of the plurality of impactor stages and the plurality of isolation stages, interposed between adjacent pairs of impactor stages, when the plurality of impactor stages and the plurality of isolation stages have been moved to their compressed states.
Figure 6:
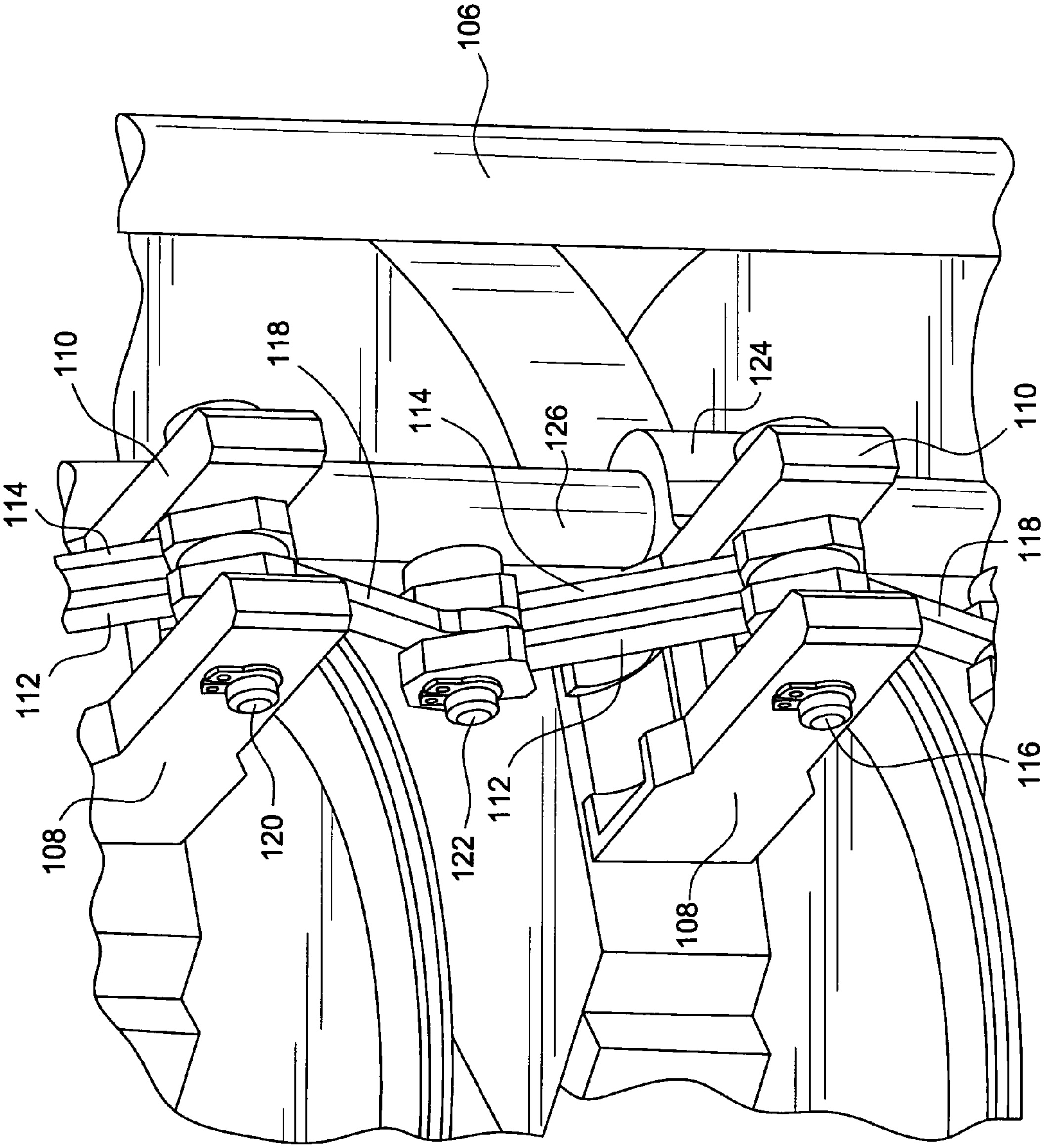
FIG. 6 is an enlarged perspective view illustrating the structural details of the linkage mechanisms of the plurality of impactor stages.
Figure 7:
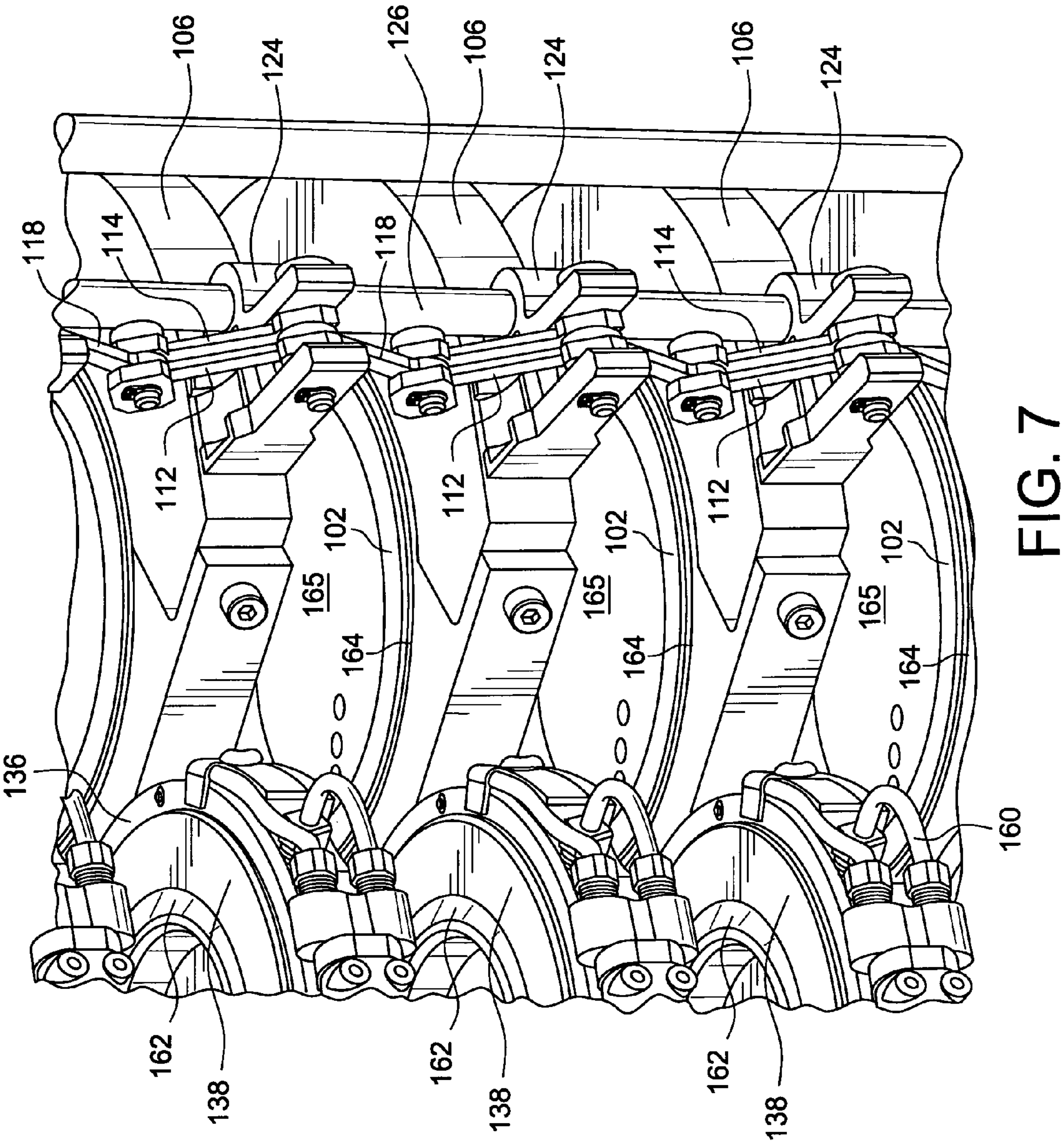
FIG. 7 is an enlarged perspective view illustrating the structural details of the impactor stages and the isolation stages, as well as the fluid conduits operatively associated with each one of the plurality of isolation stages.

Subsequently, the extension actuator 128 is again activated so as to retract the piston rod 132, and in this manner, not only are the plurality of impactor stages 102-N raised or elevated, but since the plurality of isolation stages 136-N are respectively interposed between successive or adjacent pairs of the impactor stages 102-N, all of the impactor stages 102-N and all of the isolation stages 136-N are raised or elevated and compressed together as shown in FIG. 5. In this manner, all of the isolation stages or separation stages 136-N serve to isolate each one of the plurality of impactor stages 102-N from each other. As can best be appreciated from FIG. 8, a plurality of flexible couplings 158 are respectively interposed between, and serve to operatively connect, the isolation stage housings 138 to the isolation mounting plates 140, and in this manner, the plurality of isolation or separation stages 136-N are able to be properly inserted into the spaces defined between the pairs of successive or adjacent impactor stages 102-N, and effectively aligned with the plurality of impactor stages 102-N, as illustrated within FIGS. 4 and 8. It is noted at this junction that each one of the isolation or separation stages 136-N is also provided with a pair of fluid conduits 160, as can best be seen in FIG. 7, and operatively associated valving, not shown, as a result of which, various fluids can be injected or withdrawn into or from each impactor stage 102-N sandwiched between the isolation stages 136.

For example, a collection fluid can be injected into each impactor stage 102-N so as to collect or remove the particulate matter or drug sample that has been deposited upon isolated internal surfaces or impactor plate portions of each one of the impactor stages 102-N. Still further, the fluid conduits 160 can also be utilized to inject cleaning and drying fluids into each one of the isolated impactor stages 102-N so as to clean and dry the surface portions or impact plates of the impactor stages 102-N. Still further, it is also noted, as can best be appreciated from FIG. 7, that each one of the frame members or housings 138 of the plurality of isolation stages 136-N is provided with an upper compressible sealing member 162, along the inner periphery of the frame member or housing 138, as well as a lower compressible sealing member, not visible. In a similar manner, each one of the impactor stages 102-N is provided with an upper compressible sealing member 164, along the outer periphery thereof, as well as a lower compressible sealing member, not visible. Still further, the diametrical extent of each one of the plurality of isolation stages 136-N corresponds to the diametrical extent of each one of the impactor stages 102-N such that when the plurality of impactor stages 102-N and the plurality of isolation stages 136-N are compressed together, as illustrated, for example, within FIG. 5, the compressible sealing members 162,164 disposed upon the plurality of isolation stages 136-N and upon the plurality of impactor stages 102-N will effectively cooperate together and form internal volumes 165 upon the plurality of impactor stages 102-N which are in fact isolated and sealed.

Figure 3:
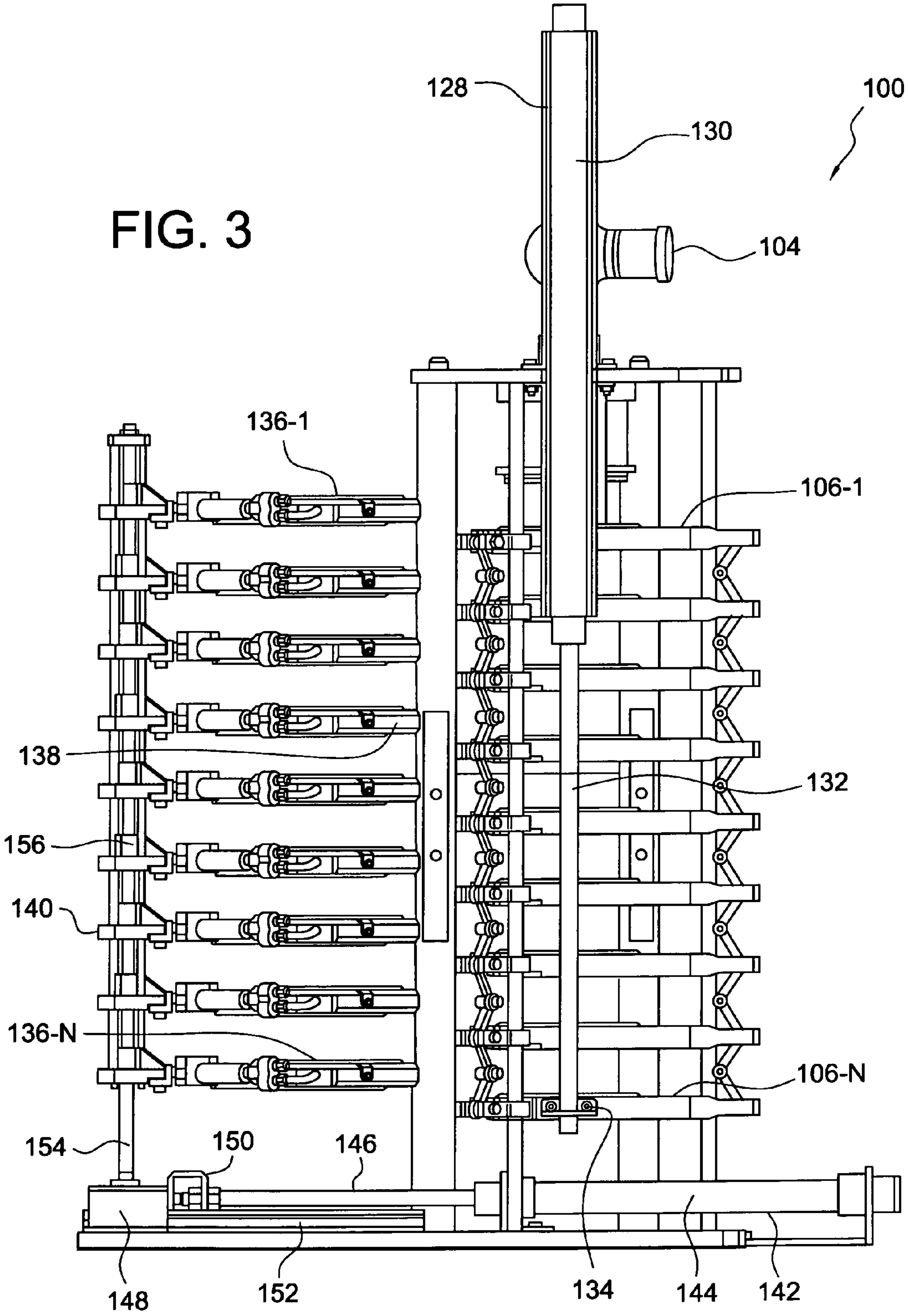
FIG. 3 is a substantially side elevational view of the automated cascade impactor as shown in FIG. 1 illustrating the plurality of impactor stages when the impactor stages are disposed in their separated states with respect to each other in preparation for the respective insertion of the plurality of isolation stages to their positions interposed between adjacent pairs of the separated impactor stages.
Figure 8:
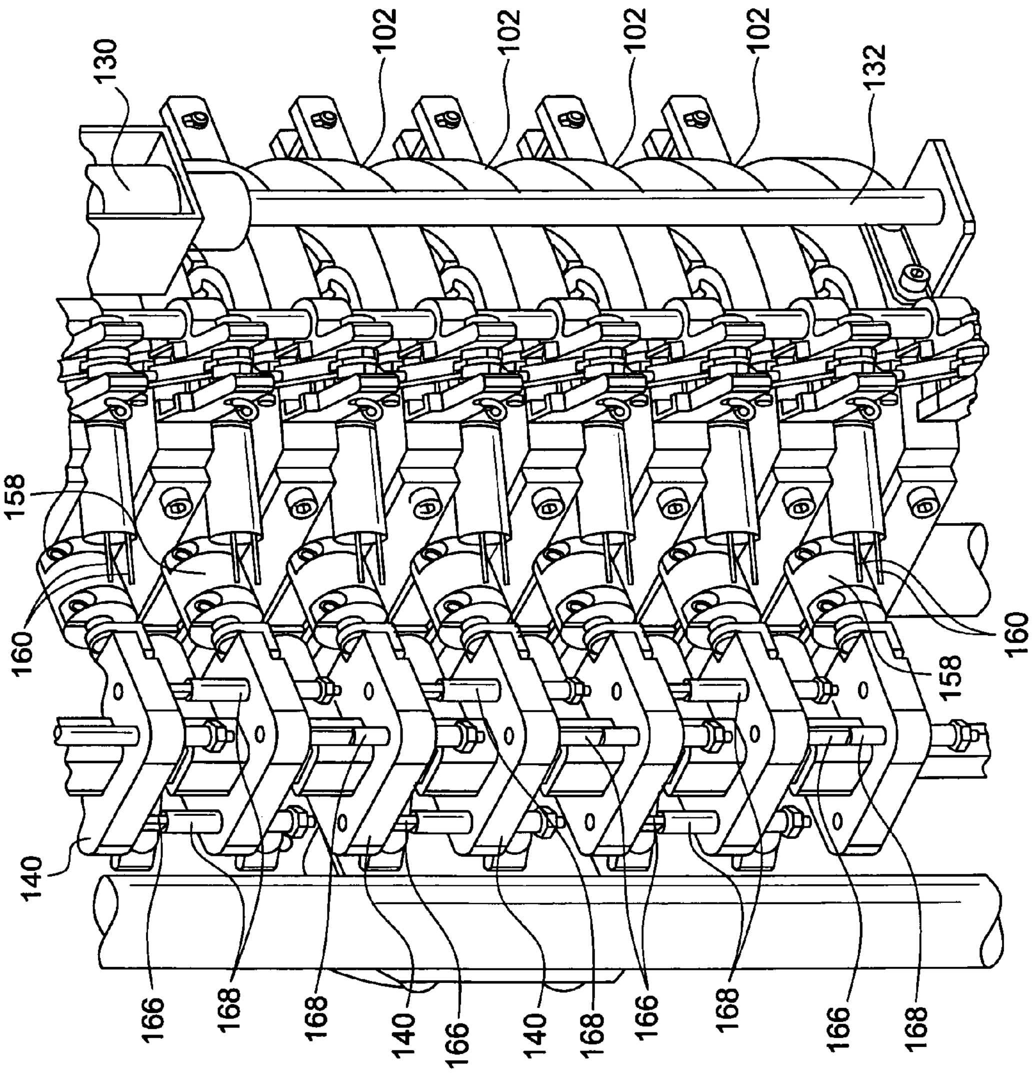
FIG. 8 is an enlarged perspective view illustrating the structural details of the isolation stages as mounted upon the isolation armature for vertical movement upwardly and downwardly along the isolation armature.

It is lastly noted, in conjunction with the vertically downward movement of the plurality of the isolation stages 136-N, after they have been removed from their collective disposition between adjacent pairs of the impactor stages 102-N, as disclosed within FIGS. 4 and 5, and returned to their original start positions, as illustrated within FIG. 3, in preparation for the initiation of a new dose determination cycle, that each one of the mounting plates 140 of the plurality of isolation stages 136-N is provided with a pair of guide shafts 166, as can best be seen in FIG. 8, which are fixedly mounted between successive mounting plates 140 with the shafts 166 disposed within diagonally opposite corner regions of each mounting plate 140 and with each alternative mounting plate 140 having the pair of guide shafts 166 disposed in alternative corner paired regions. In addition, it is seen that each guide shaft 166 is disposed within a collar 168. In this manner, the mounting plates 140 are able to move vertically upwardly and downwardly along the guide shafts 166, however, the collars 168 effectively serve as stop members for limiting the downward movement of the mounting plates 140 and their associated isolation stages 136-N. Accordingly, the plurality of isolation stages 136-N will be respectively disposed at precisely the correct elevation so as to correspond with the location of the spaces respectively defined between the plurality of impactor stages 102-N when the impactor stages 102-N are disposed in their separated states as disclosed, for example, within FIG. 3.

Having described essentially all of the primary operative components of the basic automated cascade impactor 100, a brief description of an operative cycle will now be set forth. More particularly, as can best be appreciated with reference being made to the flow chart shown in FIG. 9 and generally indicated by the reference character 200, all of the major components of the automated cascade impactor 100 are initially disposed at their respective positions as illustrated within FIG. 1, and as schematically noted in step or flow chart block 202 of the flow chart 200 of FIG. 9, the extension actuator 128 is in fact actuated such that all of the impactor stages 102 will subsequently be compressed so as to now assume their positions disclosed within FIG. 2. At this time, the automated cascade impactor 100 can measure the pressure prevailing within the internal volume defined within each compressed stage of the automated cascade impactor 100 so as to determine when the compression force is sufficient so as to form an appropriate seal between the impactor stages 102 such that particulate matter can in fact be properly dispensed into the impactor stages 102.

The control system incrementally increases the sealing force until the proper seal state is achieved. This adaptive sealing decreases the O-ring wear and tear and thus increases its service life by using only the necessary sealing force. Accordingly, as schematically illustrated or noted within step or flow chart block 204 of the flow chart 200 of FIG. 9, particulate matter is in fact dispensed into the plurality of impactor stages 102 as they are disposed in their compressed states. After this particulate matter dispensing step, the extension actuator 128 is again actuated such that the plurality of impactor stages 102 are separated from each other, as schematically noted within step 206 of the flow chart 200 of FIG. 9, so as to once again assume their relative positions illustrated within FIGS. 1 and 3.

Figure 9:
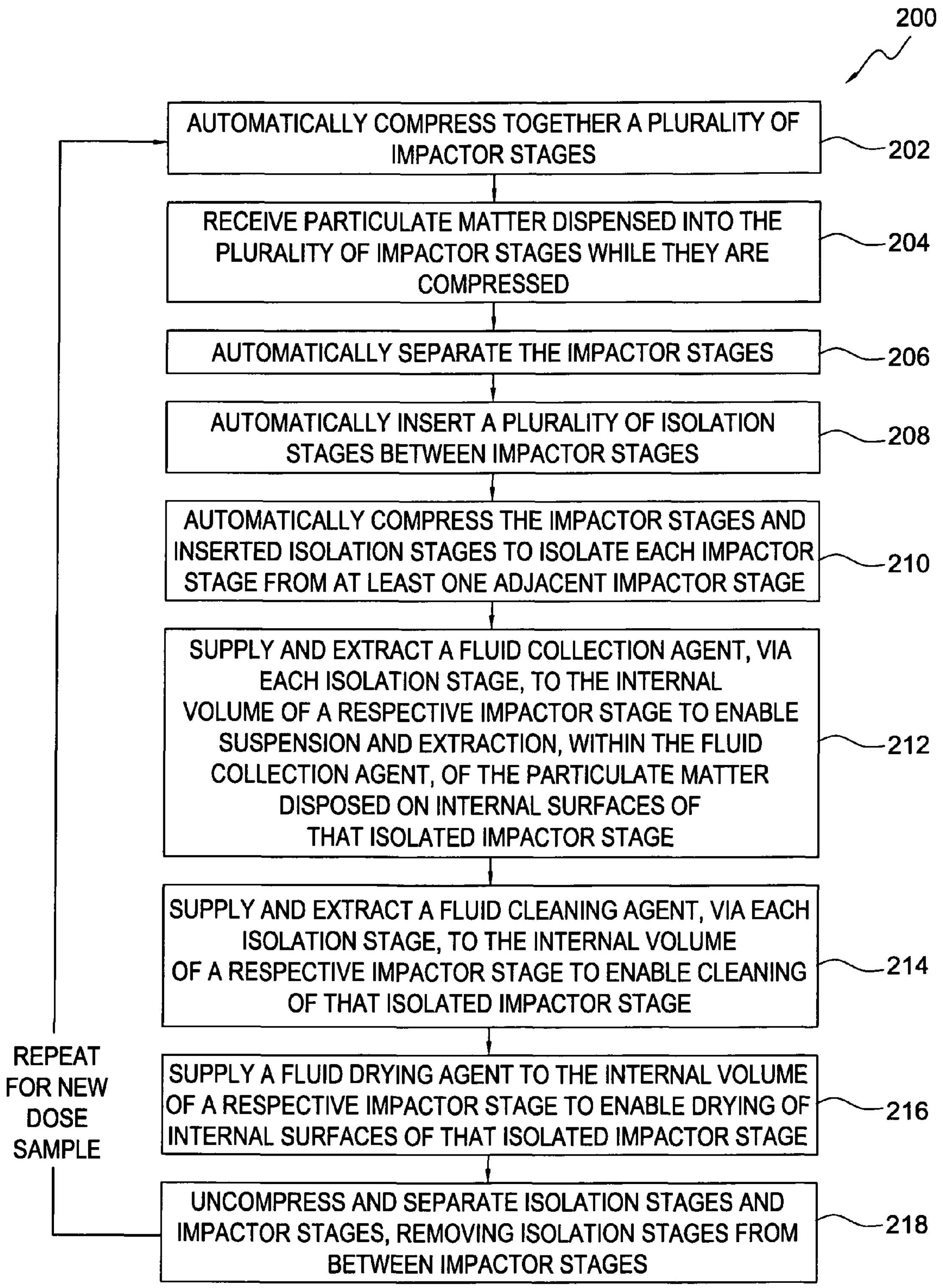
FIG. 9 is a flow chart of an operational cycle as performed by means of the automated cascade impactor.

At this point in time, the isolation actuator 142 is in fact actuated so as to respectively move the plurality of isolation stages 136 to their positions interposed between successive ones of the impactor stages 102 as schematically noted by means of step or flow chart block 208 of the flow chart 200 of FIG. 9. Subsequently, as schematically noted by means of the step or flow chart block 210 of the flow chart 200 of FIG. 9, the extension actuator 128 is again actuated in its retraction mode such that the plurality of impactor stages 102 and the plurality of isolation stages 136 are compressed together whereby each impactor stage 102 will be isolated from an adjacent or successive impactor stage 102 by means of one of the isolation stages 136. Continuing further, and while the plurality of impactor stages 102 and the plurality of isolation stages 136 are disposed at their compressed states, a fluid collection agent is dispensed, as schematically noted by means of the step or flow chart block 212 of the flow chart 200 of FIG. 9, through means of the fluid conduits 160 of each isolation stage 136 into the internal volume of each one of the impactor stages 102 so as to enable dissolution, suspension, and extraction, within the fluid collection agent, of the particulate matter previously dispensed onto the internal surface portions of the isolated impactor stages 102. During or after the dispensing of the fluid collection agent into the impact-or stages 102, the automated cascade impactor 100 can be reciprocated, shaken, or otherwise moved by a suitable agitation or oscillation mechanism, not disclosed herein but disclosed within the aforenoted parent patent and patent application, so as to shake and agitate the fluid collection agent so as to in fact aid in the removal of the particulate matter from all of the internal surface portions of the impactor stages 102 upon which such particulate matter was previously deposited.

After completion of the shaking operation, fluid samples of the dissolved drug can be collected by the operation of suitable pumps or other devices, not shown, operatively connected to the fluid conduits 160 of the isolation stages 136. As noted within step or flow chart block 214 of the flow chart 200 of FIG. 9, a fluid cleaning agent is supplied to, and thereafter extracted from, each of the internal volumes of the impactor stages 102, again by means of the fluid conduits 160 of the isolation stages 136, so as to enable cleaning of the isolated impactor stages 102. The aforenoted shaking or oscillation mechanism can also be used after the fluid cleaning agent has been supplied to the impactor stages 102 so as to facilitate the cleaning process. The extraction of the fluid cleaning agent is again conducted back out through the fluid conduits 160 by means of suitable suction or other techniques. Subsequent to the aforenoted cleaning step, a fluid drying agent is supplied to the internal volumes of the impactor stages 102, again by means of the fluid conduits 160 of the isolation stages 136, so as to enable drying of the internal surface portions of the isolated impactor stages 102. The drying agent may be in a gas or liquid state and may be conducted under high or low pressure conditions. The aforenoted shaking or oscillation mechanism can also be used during the drying step or cycle so as to likewise facilitate the drying process. Lastly, as schematically noted by means of the step or flow chart block 218 of the flow chart 200 of FIG. 9, the extension actuator 128 is again actuated to its extension state whereby all of the impactor stages 102 and all of the isolation stages 136 are decompressed such that the apparatus is effectively returned to its original position as illustrated within FIG. 1 such that the apparatus is ready for a new drug dose sample to be delivered to the impactor 100 for testing.

While the aforenoted automated cascade impactor 100 has operated quite satisfactorily, several improvements have been developed, and such improvements, being the subject matter of this continuation-in-part application, will now be described. Accordingly, with reference now being made to FIGS. 10 and 11, a new and improved automated cascade impactor is disclosed and is generally indicated by the reference character 300. It is to be noted that those component parts of the automated cascade impactor 300 which correspond to similar component parts of the automated cascade impactor 100 are designated by means of corresponding reference characters except that they are within the 300 series, while any additional components are designated by higher reference characters extending into the 400 and 500 series. More particularly, in a manner similar to automated cascade impactor 100 as illustrated, for example, within FIG. 1, the automated cascade impactor 300 is seen to comprise a vertically spaced arrangement of a plurality of impactor stages 302-1 through 302-N and a vertically spaced arrangement of a plurality of isolation stages 336-1 through 336-N. As can be more clearly seen from FIG. 11, however, and in accordance with a first significantly different and improved version of the isolation stages of the present invention automatic cascade impactor 300, when compared to the previously noted automated cascade impactor 100, each one of the isolation stages 336, such as, for example, the isolation stage 336-1, actually comprises a pair of isolation stages, that is, an upper isolation stage 336-1-U and a lower isolation stage 336-1-L. Accordingly, as disclosed, for example, within, and as can be best appreciated from, FIG. 11, when the plurality of impactor stages 302 and the plurality of isolation stages 336 are moved toward each other so as to be interdigitated with respect to each other in a manner similar to the disposition of the impactor stages 106 and the isolation stages 136 as disclosed within FIGS. 4 and 5, each pair of the isolation stages 336, that is, an upper isolation stage 336-U and a lower isolation stage 336-L, are interposed between successive ones of the impactor stages 302-1 through 302-N, while at the same time, each one of the impactor stages 302, such as, for example, the uppermost impactor stage 302-1, is interposed between the lower isolation stage 336-1-L of the uppermost pair of isolation stages 336, and the upper isolation stage 336-2-U of the next or successive pair of isolation stages 336-2. It is also to be noted that the lowermost structure operatively associated with the plurality of impactor stages 302, as illustrated within FIG. 11, is not actually an impactor stage but is a filter assembly 369 for collecting any drug that has not been collected upon the impactor stages 302. Typically, the filter assembly 369 may comprise, for example, a suitable fibrous material or a very fine stainless steel mesh.

Figure 12:
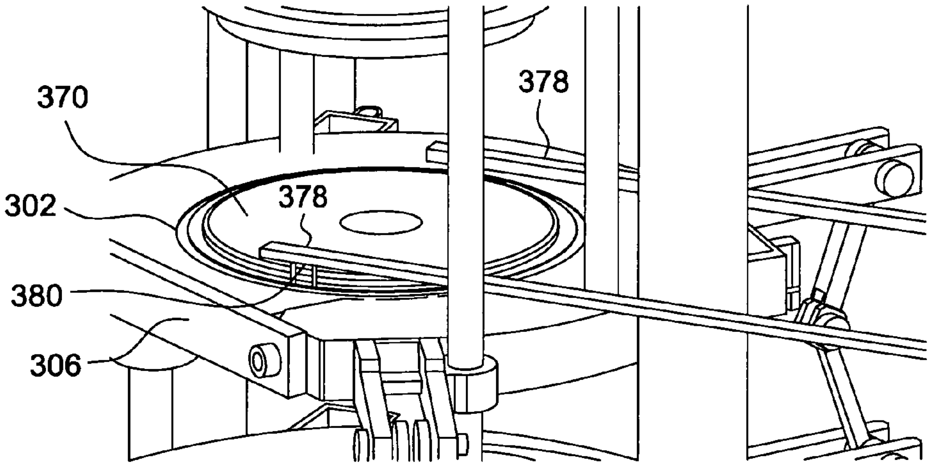
FIG. 12 is an enlarged perspective view of one of the impactor stages of new and improved automated cascade impactor as disclosed in FIG. 10 showing the disposition of an impactor plate within the impactor stage and the disposition of the gripper arms of the gripper arm assembly which is used to transfer the impactor plate back and forth between the impactor stage and one of the isolation stages.
Figure 13:
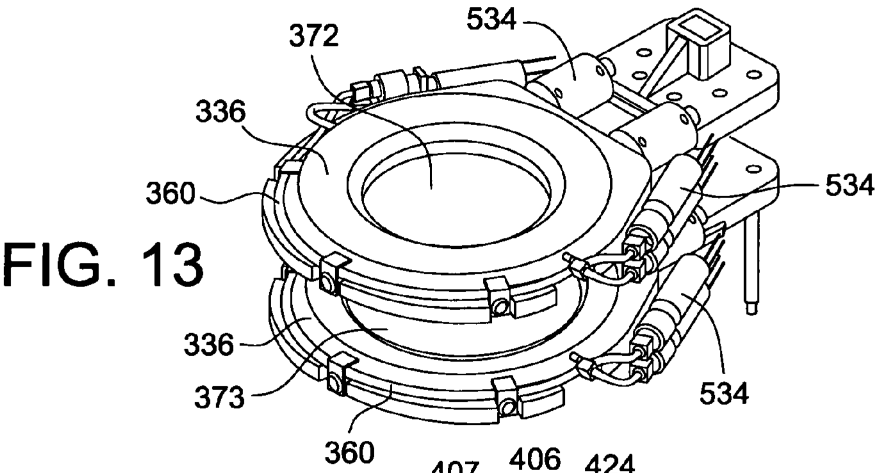
FIG. 13 is an enlarged perspective view of a pair of the isolation stages of new and improved automated cascade impactor as disclosed in FIG. 10 showing the centrally recessed portions of the isolation stages within which one of the impactor plates will be disposed.

In addition, as can best be appreciated from FIG. 12, each one of the impactor stages 302 actually has an impactor plate 370 removably disposed therewithin, and in a similar manner, as can best be seen within, and appreciated from FIG. 13, each one of the upper isolation stages 336-U is provided with a centrally recessed portion 372, while each one of the lower isolation stages 336-L is provided with a centrally recessed portion 373 within which an impactor plate 370, having been removed from a particular one of the impactor stages 302 as will be more fully discussed hereinafter, will be disposed. The reasons for employing an isolation stage system comprising the pairs of isolation stages 336-U, 336-L, as well as the employment of removable impactor plates 370, are several.

Firstly, such structural combination renders the overall system substantially more economical and environmentally friendly. This is because, as can be readily appreciated from FIG. 13, the surface areas or volumes of the centrally recessed portions 373 of the isolation stages 336 are for housing or accommodating one of the impactor plates 370, whereas the annular surface portions of the isolation stages 336, surrounding or defining the centrally recessed portions 372, house or confine the impactor stages 302 therebetween. Accordingly, the drug collection processes for the drug disposed upon the impactor plates 370, can be obtained separately from the drug collection processes for the drug disposed upon the impactor stages 302. Accordingly, if only one of these drug collection processes is to be implemented for a particular reason or type of data collection, the amount of solvent used is considerably reduced. Secondly, when both drug collection processes are in fact implemented, such procedures provide the technician with greater data differentiation.

Figure 10:
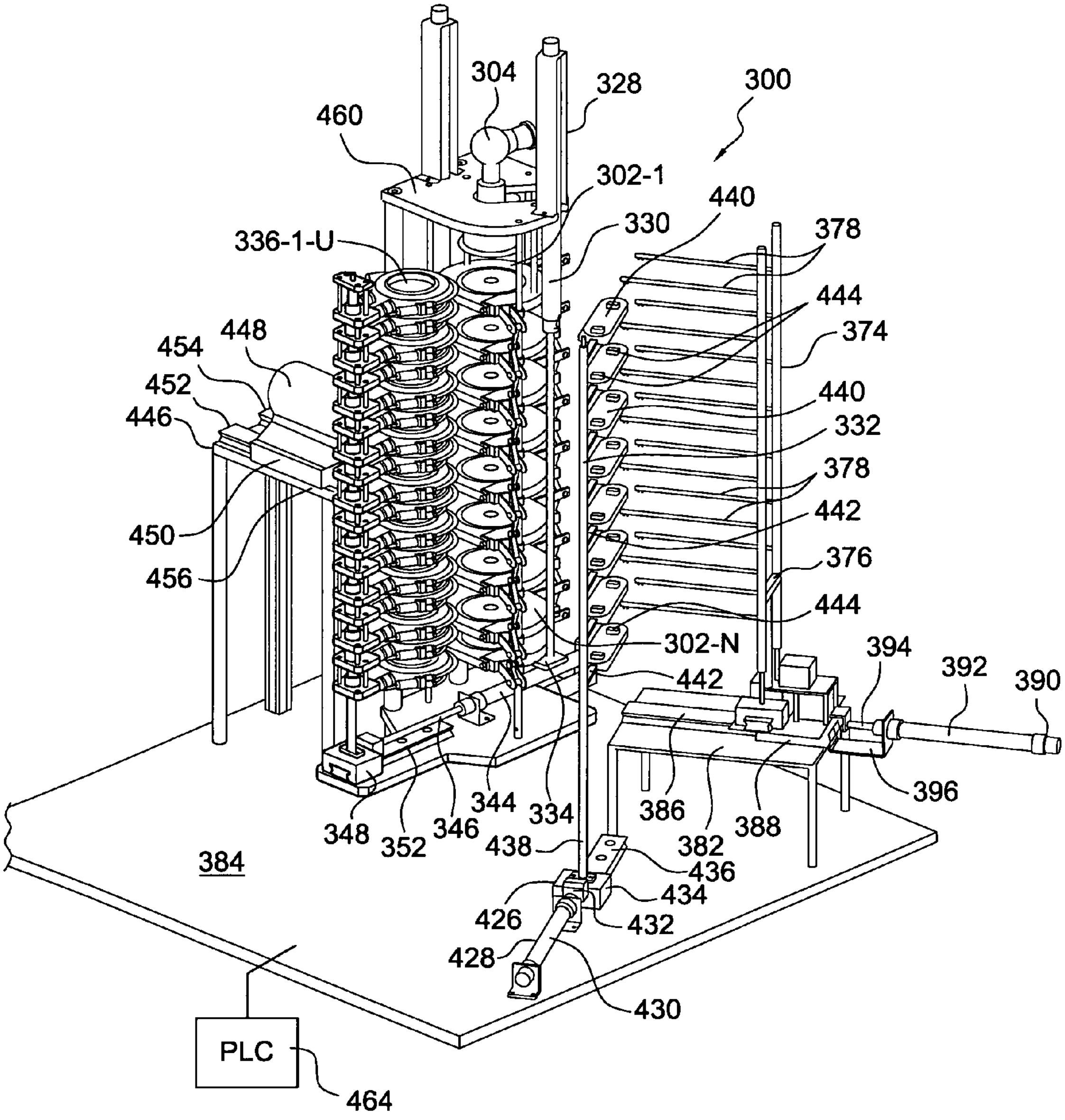
FIG. 10 is a perspective view of a new and improved automated cascade impactor developed in accordance with the principles and teachings of the present invention and disclosing the various operative components thereof.
Figure 11:
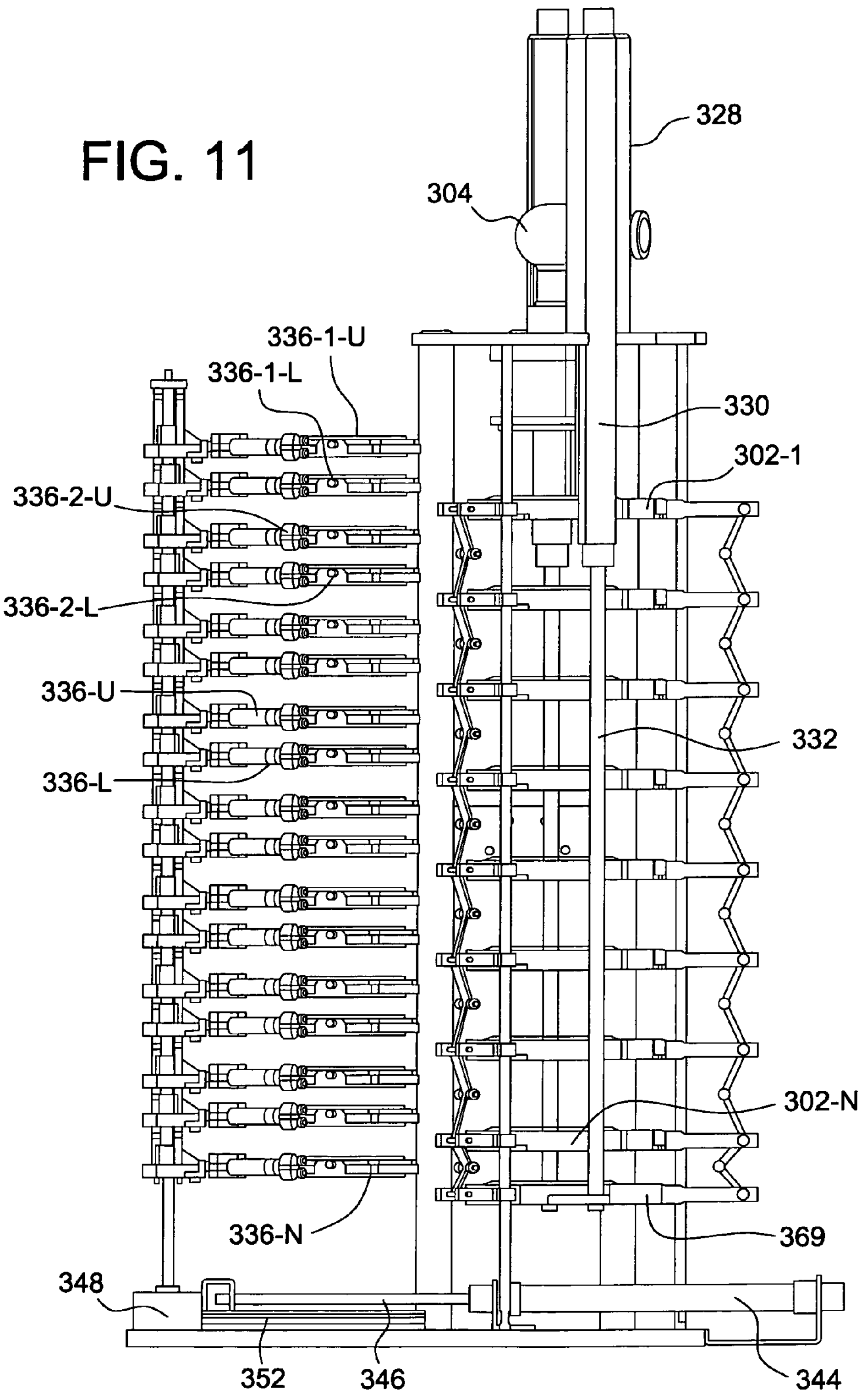
FIG. 11 is a partial side elevational view of the new and improved automated cascade impactor as disclosed in FIG. 10 and showing the vertically spaced arrangement of the plurality of impactor stages disposed adjacent to the vertically spaced arrangement of the plurality of isolation stages.
Figure 14:
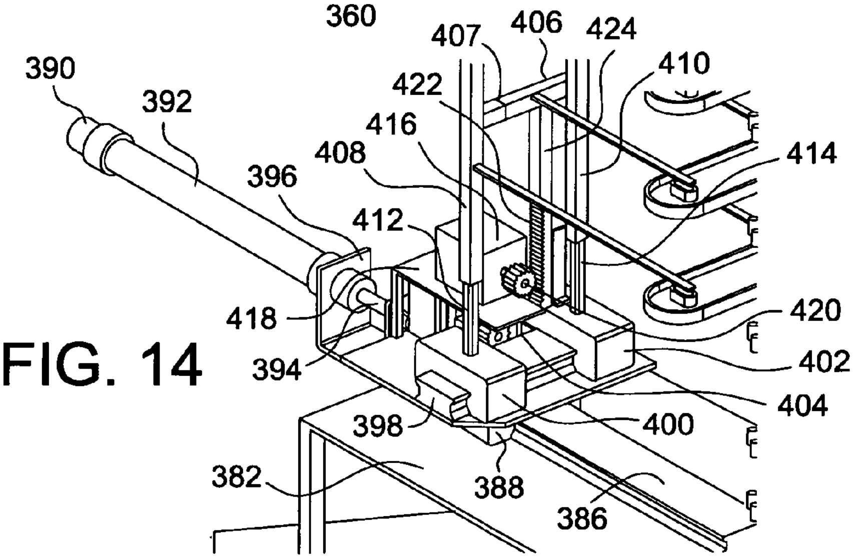
FIG. 14 is enlarged partial perspective view of the drive mechanisms of the gripper arm assembly of the new and improved automated cascade impactor as disclosed in FIG. 10 showing the details of the various drive mechanisms of the gripper arm assembly in order to properly position the gripper arms with respect to the impactor plate in order to properly transfer the same between its aforenoted two positions.

Continuing further, and with reference now being made to FIGS. 10,12, and 14, there is disclosed an impactor plate gripper arm assembly 374 which is adapted to effectively pick up the plurality of impactor plates 370 from the plurality of impactor stages 302 and transfer them into the plurality of centrally recessed portions 373 of the isolation stages 336, and conversely, to pick up the plurality of impactor plates 370 from the isolation stages 336 and transfer them back to the impactor stages 302. More particularly, the impactor plate gripper arm assembly 374 is seen to comprise an upstanding H-shaped framework 376 from which project vertically spaced pairs of impactor plate gripper arms 378 which are fixedly mounted upon the H-shaped framework 376. At the distal end portion of each impactor plate gripper arm 378 there is provided a dependent impactor plate gripper arm pin 380, and as can best be appreciated from FIG. 12, when the impactor plate gripper arms 378 are disposed within the vicinity of the impactor plate 370, so as to remove the same from the impactor stage 302, the impactor plate gripper arm pins 380, dependent from the pair of impactor plate gripper arms 378, will engage diametrically opposed external surface portions of the impactor plate 370 so as to in fact clamp the impactor plate 370 between the impactor plate gripper arm pins 380 in preparation for the aforenoted transfer procedure from the impactor stage 302 to the appropriate recessed portion 373 of the isolation stage 336. It is to be noted that in order for the plurality of gripper arms 378 to perform their various functions with respect to, for example, particular impactor plates 370, the plurality of gripper arms 378 must undergo linear movements with six degrees of freedom, that is, they must undergo forward and backward, or leftward and rightward, movements as can be appreciated from FIGS. 10 and 14, they must undergo upward and downward movements, and they must undergo lateral movements toward and away from each other. More particularly, it is seen that the impactor plate gripper arm assembly 374 is mounted upon a suitable base framework 382, and that the base framework 382 is, in turn, fixedly mounted upon a suitable floor or foundation 384. A first linear guide rail 386 is fixedly mounted upon the base framework 382, and a first linear slide block 388 is slidably mounted upon the first linear guide rail 386. A suitable actuator 390, which may comprise a cylinder 392 and a piston rod 394, is fixedly connected to the first linear slide block 388 by means of a mounting bracket 396, and in this manner, when the piston rod 394 is extended, the linear slide block 388 moves toward the left upon the first linear guide rail 386 as viewed in FIG. 10, while when the piston rod 394 is retracted, the first linear slide block 388 moves toward the right upon the linear guide rail 386 as viewed in FIG. 10. Accordingly, it can be appreciated that the plurality of impactor plate gripper arms 378 will move toward and away from the impactor stages 302 within which the impactor plates 370 are disposed.

In a similar manner, a second linear guide rail 398 is mounted upon the first linear slide block 388 such that the longitudinal orientation of the second linear guide rail 398 is disposed transversely with respect to the longitudinal orientation of the first linear guide rail 386. In addition, a pair of second linear slide blocks 400,402 are slidably mounted upon the second linear guide rail 398. It is seen that lower end leg portions of the H-shaped framework 376 are fixedly mounted within the pair of second linear slide blocks 400,402, and a suitable motor drive 404, which may comprise, for example, a motor drive shaft and a pair of oppositely disposed rack and pinion assemblies, not shown, is provided such that when the motor drive 404 is disposed in a first rotary mode, the pair of second linear slide blocks 400,402 will move toward each other, and when the motor drive 404 is disposed in a second rotary mode, the pair of second linear slide blocks 400,402 will move away from each other. Accordingly, the impactor plate gripper arms 378 will likewise move toward and away from each other. To in fact permit such movements to occur, it is also noted that the cross-bar 406 of the H-shaped framework 376 actually comprises a telescopic structure, as shown at 407, which will permit the left and right upstanding members 408,410 of the H-shaped framework 376 to move toward and away from each other.

Lastly, and in a similar manner, in order to permit the H-shaped framework 376 to move upwardly and downwardly so as to properly position the elevational levels of the plurality of impactor plates 370 relative to the isolation stages 336 and the recessed portions 373 into which the impactor plate 370 are to be placed, it is noted that the left and right upstanding members 408,410 of the H-shaped framework 376 are likewise telescopically mounted upon lower end portions 412, 414 which are fixedly mounted within the second linear slide blocks 400,402. A motor drive 416 is mounted upon a platform 418 which is mounted upon the first linear slide block 388, and the output shaft of the motor drive 416 is provided with a pinion 420. In turn, the pinion 420 is engaged with an upstanding rack 422 which is formed within the lower end portion of a vertically oriented standard or post 424 that is fixedly connected to an undersurface portion of the cross bar 406 of the H-shaped frame-work 376 of the impactor plate gripper arm assembly 374. Accordingly, when the motor drive 416 is rotatably operated in a first mode so as to rotate the pinion 420 in, for example, the clockwise direction as illustrated within FIG. 14, the rack 422 will be lowered thereby lowering the H-shaped frame-work 376 and the impactor plate gripper arms 378, whereas conversely, when the motor drive 416 is rotatably operated in a second mode so as to rotate the pinion 420 in, for example, the counterclockwise direction as illustrated within FIG. 14, the rack 422 will be elevated thereby elevating the H-shaped framework 376 and the impactor plate gripper arms 378.

With reference again being made to FIG. 10, it is also seen that an impactor plate gripper arm pin wash assembly 426 is provided for washing the impactor plate gripper arm pins 380 whereby the pins 380 will be cleaned after each operative cycle such that cross-contamination does not occur between drug dosing cycles. More particularly, it is seen that the impactor plate gripper arm pin wash assembly 426 comprises a linear actuator 428 which comprises a cylinder 430 and a piston rod, not visible. The distal end of the piston rod, not visible, is fixedly connected to a bracket 432 which, in turn, is fixedly mounted upon a third linear slide block 434 which is slidably mounted upon a third linear guide rail 436. An upstanding tubular member 438 has its lower end portion fixedly mounted within the third linear slide block 434, and it is understood that the tubular member 438 is adapted to conduct washing fluid bi-directionally therewithin. A plurality of impactor plate gripper arm washing plates 440 are fixedly mounted upon the upstanding tubular member 438 at spaced intervals, corresponding to the vertical spacing defined between the successive pairs of the impactor plate gripper arms 378, by means of short tubular shafts 442, and it is further seen that a pair of washing wells 444 are defined upon each one of the washing plates 440 for receiving a respective one of the impactor plate gripper arm pins 380. The washing wells 444 extend above the planes of the washing plate 440 such that the washing fluid disposed within the washing wells 444 can overflow the same, flow into the washing plates 440 which have peripheral containment lips disposed thereon and from which the washing fluid can be conducted away by means of other fluid conduits, not shown.

In this manner, the actual washing fluid which comes into contact with the impactor plate gripper arm pins 380 will always be fresh and clean. It can of course also be appreciated that when the piston rod, not visible, is disposed at its retracted position, as it is in FIG. 10, the third linear slide block 434 is disposed at its retracted position whereby the upstanding tubular member 438, the washing plates 440, and washing wells 444 will be disposed remote from the impactor plate gripper arms 378 and the impactor plate gripper arm pins 380, whereas, when the piston rod, not visible, is disposed at its extended position, the third linear slide block 434 will be disposed at its extended position whereby the upstanding tubular member 438, the washing plates 440, and the washing wells 444 will be disposed adjacent to the impactor plate gripper arms 378 and the impactor plate gripper arm pins 380 such that a washing operation can be implemented when the impactor plate gripper arm pins 380 are lowered into the washing wells 444.

Figure 15:
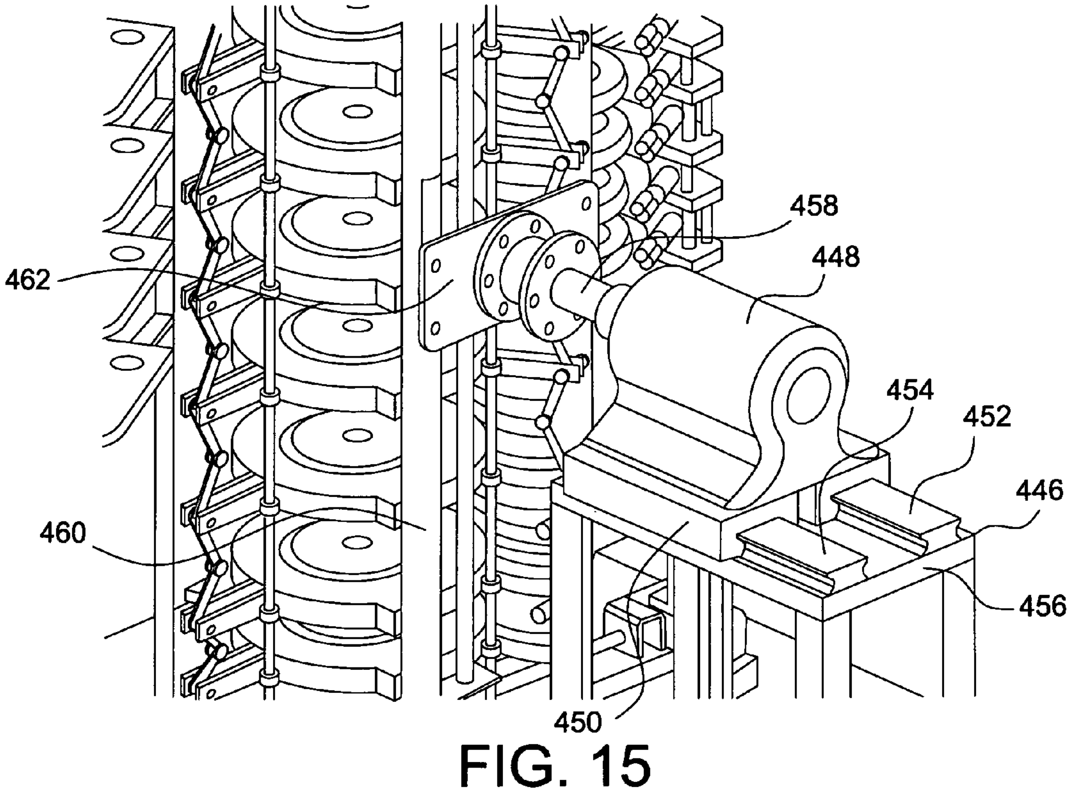
FIG. 15 is a partial perspective view of a combination rotary drive and linear reciprocator assembly operatively connected to the automated cascade impactor so as to impart rotation and reciprocal movements to the automated cascade impactor in order to promote the full and complete dispersal of all of the fluids introduced into the automated cascade impactor, such as, for example, the fluid collection agents or drug solvents, the cleaning fluids, the drying agents, and the like, throughout the impactor stages and the isolation stages.

With reference now being made to FIGS. 10 and 15, it is seen still further that the new and improved automated cascade impactor 300 also includes a combination rotary drive and linear reciprocator assembly 446 operatively connected to the automated cascade impactor 300 so as to impart rotation and reciprocal movements to the automated cascade impactor 300 in order to promote the full and complete dispersal of all of the fluids introduced into the automated cascade impactor 300, such as, for example, the fluid collection agents or drug solvents, the cleaning fluids, the drying agents, and the like, throughout the impactor stages 302 and the isolation stages 336, as will be more fully disclosed and described hereinafter. More particularly, as can best be seen from FIG. 15, the combination rotary drive and linear reciprocator assembly 446 comprises a rotary drive motor 448, the base 450 of which effectively forms a linear slide block which is mounted upon a pair of linear guide rails 452,454. The pair of linear guide rails 452,454 are fixedly mounted upon an elevated platform 456, and it is seen that the rotary output shaft 458 of the rotary drive motor 448 is fixedly connected to a framework 460, upon which the plurality of impactor stages 302 and the plurality of isolation stages 336 are mounted, by means of a mounting bracket or mounting plate 462. When the framework 460, the plurality of impactor stages 302, and the plurality of isolation stages 336 are so mounted upon the rotary drive motor 448 by means of the mounting bracket 462, it is to be noted that the entire assembly comprising the framework 460, the plurality of impactor stages 302, and the plurality of isolation stages 336 will be disposed above the floor or foundation 384 so as to permit the assembly, comprising the framework 460, the plurality of impactor stages 302, and the plurality of isolation stages 336, to be freely rotated, inverted, or the like, without interference with the floor or foundation 384.

Figure 16:
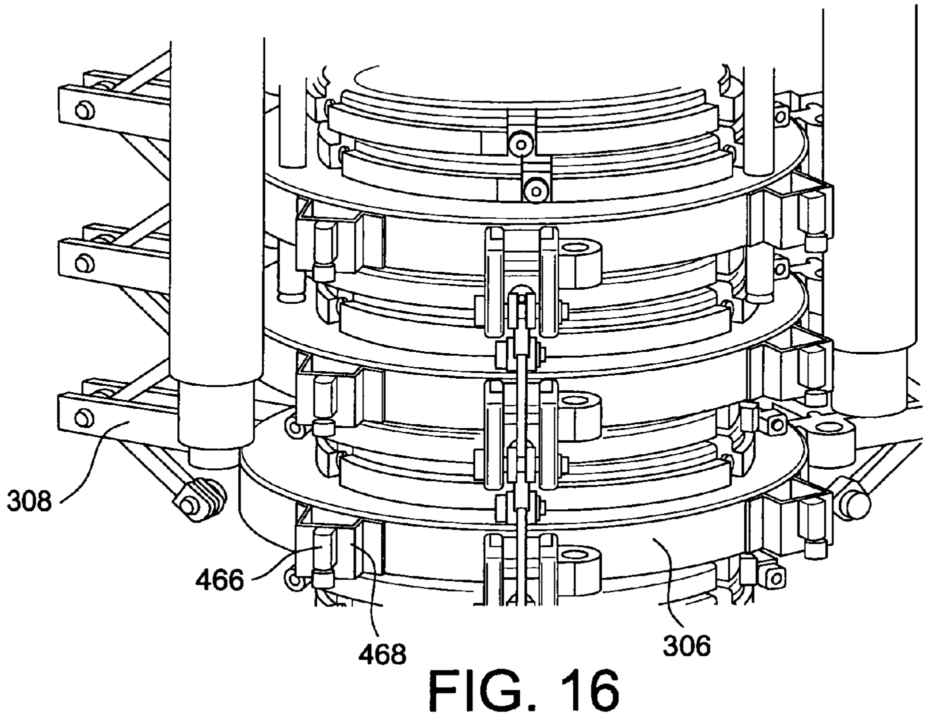
FIG. 16 is a partial perspective view of the impactor stages showing the mounting thereon of auxiliary vibrators for enhancing the turbulence of the various fluids caused by the aforenoted combination rotary drive and linear reciprocator assembly.

A suitable linear actuator, not shown, can be operatively connected to the rotary drive motor 448 so as to in fact cause the same to undergo reciprocal linear movements along the linear guide rails 454,454 in addition to its rotary movements. It is to be further understood that all movements of all of the structural components disclosed and described hereinabove, as well as all fluid controls, which will be more fully disclosed hereinafter, can be under the control of a suitable computer-control system, such as, for example, a programmable logic computer or PLC schematically denoted at 464. Still yet further, as can be seen in FIG. 16, and in conjunction with the aforenoted use of the combination rotary drive and linear reciprocator assembly 446, individual vibrators 466 may be mounted upon each one of the impactor stages 302 so as to further ensure the proper dispersal and mixing of the particular fluids inside the isolation stages 336. The vibrators 466 are mounted upon suitable mounting brackets 468 which are attached to external surface portions of each one of the frame members or housings 306 of the plurality of impactor stages 302. Additional vibrators can also be incorporated up-on each one of the isolation stages 336, and the number of vibrators utilized per impactor or isolation stage 302,336 may vary.

Figure 17:
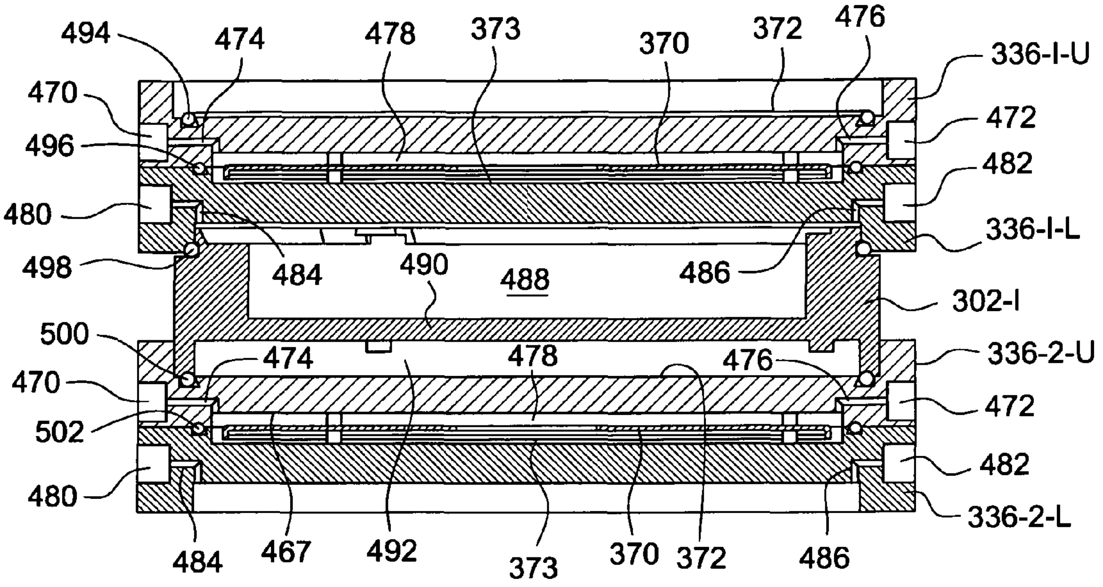
FIG. 17 is a cross-sectional view taken through the uppermost pair of isolation stages, the uppermost one of the impactor stages, and the second pair of isolation stages, and along a first plane so as to clearly disclose the solvent ports fluidically connected to the uppermost pair of isolation stages, the uppermost one of the impactor stages, and the second pair of isolation stages.

With reference now being made to FIG. 17, the introduction of the various fluids into and out of the plurality of impactor stages 302 and the plurality of isolation stages 336 will now be disclosed and described. It is initially noted, for example, as can be more readily or best appreciated from FIG. 17, that the centrally located recessed portions 372,373 respectively defined within the upper and lower isolation stages 336-U,336-L are different in structure because they serve different purposes. The centrally located recessed portion 372 of each upper isolation stage 336-U serves to accommodate the lower peripheral portion of one of the impactor stages 302, whereas an undersurface portion 467 of each upper isolation stage 336-U is also recessed so as to effectively cooperate with the recessed portion 373 of a lower isolation stage 336-L in order to accommodate or seat the impactor plate 370 therewithin. In a similar manner, an undersurface portion 469 of each one of the of the lower isolation stages 336-L is recessed so as to accommodate or seat the upper peripheral portion of the impactor stage 302. In addition, with respect to the discussion of the fluid flow paths within the various isolation stage members 336, it is seen that FIG. 17 is a cross-section of, for example, the uppermost pair of isolation stages 336-1-U,336-1-L, the second pair of isolation stages 336-2-U,336-2-L, the uppermost impactor stage 302-1 which is interposed between the uppermost pair of isolation stages 336-1-U,336-1-L and the second pair of isolation stages 336-2-U,336-2-L, the impactor plate 370, which has been removed from the uppermost impactor stage 302-1 and sandwiched between the upper isolation stage 336-1-U and the lower isolation stage 336-1-L of the uppermost pair of isola-tion stages 336-1-U,336-1-L, and the impactor plate 370 which has been removed from the second impactor stage 302-2 and sandwiched between the upper isolation stage 336-2-U and the lower isolation stage 336-2-L of the second pair of isolation stages 336-1-U,336-1-L.

Still further, it is also seen that each one of the upper isolation stages 336-1-U and 336-2-U is provided with a pair of diametrically opposite solvent ports 470,472, and auxiliary fluid passageways 474, 476, one for the injection of the solvent into, for example, the space or chamber 478 within which the impactor plate 370 is disposed, and one for the extraction of the solvent out from the space or chamber 478. The solvents within the isolation stages 336, such as, for example, within the end portions thereof as disclosed at 474, 476, are provided so as to prevent the occurrence of dead volumes within the isolation stages 336 and thus facilitate the extraction of all of the fluids therefrom. In a similar manner, it is seen that each one of the lower isolation stages 336-1-L and 336-2-L is provided with a pair of diametrically opposite solvent ports 480,482, and auxiliary fluid passageways 484, 486, one for the injection of the solvent into, for example, the upper or large space or chamber 488 of the uppermost impactor stage 302-1, and one for the extraction of the solvent out from the upper or large space or chamber 488. It is to be noted that there are also a multitude of small holes, bores, or apertures, not shown, defined within the wall 490 separating the upper or large space or chamber 488 from a lower or small space or chamber 492 of the impactor stage 302 so as to permit fluidic communication between the upper or large space or chamber 488 and the lower or small space or chamber 492 for reasons that will be explained shortly hereafter. Lastly, a plurality of O-ring seal members 494,496,498,500, and 502 are provided upon the uppermost pair of isolation stages 336-1-U,336-1-L and the second pair of isolation stages 336-2-U,336-2-L as may be deemed necessary or required.

Figure 18:
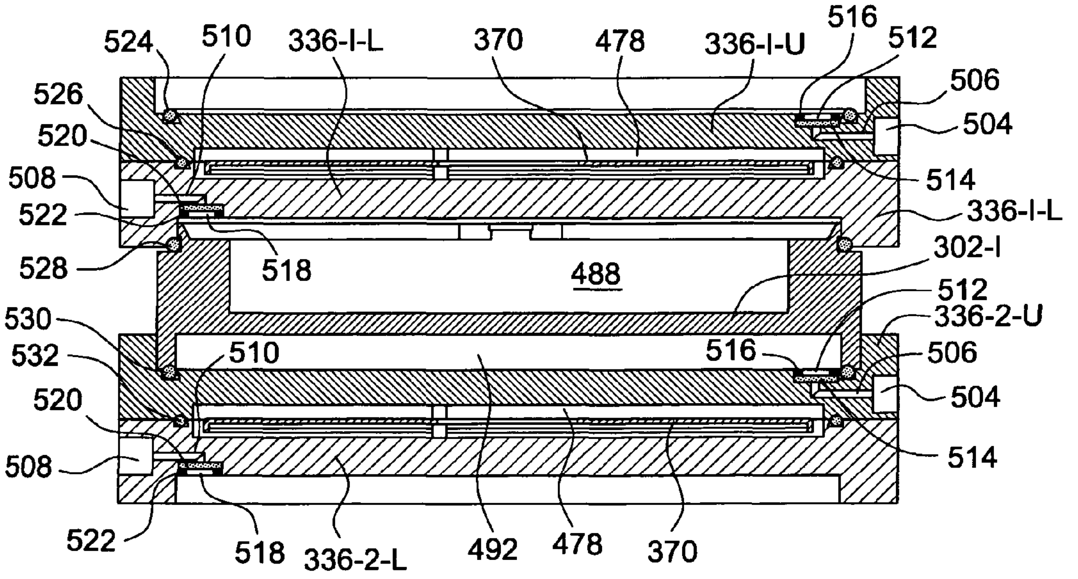
FIG. 18 is a cross-sectional view taken through the uppermost pair of isolation stages, the uppermost one of the impactor stages, and the second pair of isolation stages, and along a second plane so as to clearly disclose the air-vacuum ports fluidically connected to the uppermost pair of isolation stages, the uppermost one of the impactor stages, and the second pair of isolation stages.

With reference now lastly being made to FIG. 18, the new and improved automated cascade impactor 300 also provides for the introduction of pressurized air and vacuum conditions into and out of the plurality of impactor stages 302 and the plurality of isolation stages 336. More particularly, FIG. 18, in a manner similar to that of FIG. 17, is a cross-section of, for example, the uppermost pair of isolation stages 336-1-U,336-1-L, the second pair of isolation stages 336-2-U,336-2-L, the uppermost impactor stage 302-1 which is interposed between the uppermost pair of isolation stages 336-1-U,336-1-L and the second pair of isolation stages 336-2-U,336-2-L, the impactor plate 370, which has been removed from the uppermost impactor stage 302-1 and sandwiched between the upper isolation stage 336-1-U and the lower isolation stage 336-1-L of the uppermost pair of isolation stages 336-1-U, 336-1-L, and the impactor plate 370 which has been removed from the second impactor stage 302-2 and sandwiched between the upper isolation stage 336-2-U and the lower isolation stage 336-2-L of the second pair of isolation stages 336-1-U,336-1-L, however, unlike the cross-sectional cut or plane effectively illustrated within FIG. 17 in order to illustrate the various solvent ports 470,472,480,482, the cross-sectional cut or plane effectively illustrated in FIG. 18 is provided for illustrating the various pressurized air and vacuum ports defined within the upper and lower isolation stages 336-U,336L.

More particularly, it is seen that each one of the upper isolation stages 336-1-U and 336-2-U is provided with a pressurized air/vacuum port 504, and a first auxiliary fluid passageway 506, at a predetermined diametrical position, while each one of the lower isolation stages 336-1-L and 336-2-L is similarly provided with a pressurized air/vacuum port 508, at a diametrically opposite position along with and a second auxiliary fluid passageways 510. In addition, it is also seen that each one of the first auxiliary fluid passageways 506 of the upper isolation stages 336-1-U,336-2-U has a third auxiliary fluid passageway 512 fluidically connected thereto, and that a frit/membrane 514 is disposed within each third auxiliary fluid passageway 512. Each one of the frits or membranes 514 comprises a mesh structure so as to only permit air to fluidically pass therethrough but to effectively block the passage therethrough of any liquids. The frits or membranes 514 are retained in place within the third auxiliary fluid passageways 512 by means of a suitable retaining ring 516. In a similar manner, it is likewise seen that each one of the second auxiliary fluid passageways 510 of the lower isolation stages 336-1-L,336-2-L has a fourth auxiliary fluid passageway 518 fluidically connected thereto, and that a frit 520 is fixedly secured within the fourth auxiliary fluid passageway 512 by means of a suitable retaining ring 522. As was also the case of the cross-sectional structure illustrated within FIG. 17 in connection with the solvent ports 470,472,480,482, a plurality of O-ring seal members 524,526,528,530, and 532 are provided upon the uppermost pair of isolation stages 336-1-U,336-1-L and the second pair of isolation stages 336-2-U, 336-2-L as may be deemed necessary or required.

It is to be noted that when the solvents are to be injected into the chambers 488,492 containing the impactor stages 302, in order for the solvent to effectively migrate from one side of the impactor stage 302 to the other side of the impactor stage 302, the solvent must traverse the multitude of small holes, not shown, defined within the wall of the impactor stage 302 separating the large chamber 488 from the small chamber 492. Solvents with relatively high surface tension, such as, for example, aqueous solvents, are not able to readily migrate through the holes or pores of the wall of the impactor stage 302 separating the large chamber 488 from the small chamber 492 whereby the collection efficiency of the drug deposited upon the two sides of the impactor stage 302 will be adversely affected. Accordingly, the utilization of the pressurized air/vacuum port system of the present invention dramatically increases this drug collection efficiency. More particularly, assuming for example that the solvent is disposed within the large chamber 488 of the impactor stage 302, then vacuum conditions will effectively be applied to vacuum port 504 on the small chamber side of the impactor stage 302 while pressurized air will effectively be applied to vacuum port 508 on the large chamber side of the impactor stage 302. In this manner, a significant pressure differential is effectively established such that the solvent can in fact traverse, cross over, or pass through the holes or pores defined within the wall of the impactor stage 302 separating the large chamber 488 from the small chamber 492. It is to be further noted that when the automated cascade impactor 300 is inverted, such as, for example, by means of the rotary motor drive 448 as disclosed within FIG. 15, the different pressurized air and vacuum ports are effectively reversed so as to once again achieve a positive flow of the solvent across the barrier defined by means of the wall of the impactor stage 302 separating the large chamber 488 from the small chamber 492. To achieve the various control operations of the various fluids into and out from the isolation stages 336, the isolation stages 336 are provided with suitable integrated valves 534 which are illustrated within FIG. 13. As was previously noted, the control of such valves 534, as is true of the control of all other structural and fluid controls of the various components comprising the automated cascade impactor 300 is under the control of the programmable logic controller (PLC) 464.

Obviously, many variations and modifications of the present invention are possible in light of the above teachings. It is therefore to be understood that within the scope of the appended claims, the present invention may be practiced otherwise than as specifically described herein.

What is claimed as new and desired to be protected by Letters Patent of the United States of America, is:

1. An automated cascade impactor, comprising:

a vertical array of a plurality of impactor stages; and a vertical array of a plurality of isolation stages comprising vertically arranged pairs of isolation stages, wherein each pair of said vertically arranged pairs of isolation stages comprises an upper isolation stage and a lower isolation stage;

whereby, when said plurality of impactor stages and said plurality of isolation stages are moved toward each other in an interdigitated manner, each pair of said plurality of isolation stages is interposed between successive impactor stages of said plurality of impactor stages, while at the same time, each impactor stage of said plurality of impactor stages is interposed between a lower isolation stage of an upper pair of said plurality of isolation stages and an upper isolation stage of a successively lower pair of said plurality of isolation stages.

2. The automated cascade impactor as set forth in claim 1, wherein:

each one of said plurality of impactor stages comprises an impactor plate;

each one of said upper and lower isolation stages of a pair of isolation stages has a centrally recessed portion defined therein for receiving one of said impactor plates from one of said plurality of impactor stages; and a gripper arm assembly is provided for gripping said impactor plates, disposed within said plurality of impactor stages, and transferring said impactor plate from said plurality of impactor stages to said centrally recessed portions defined within said plurality of isolation stages, whereby, when said plurality of impactor stages and said plurality of said plurality of isolation stages are moved toward each other in an interdigitated manner, each pair of said plurality of isolation stages, that is, an upper isolation stage and a lower isolation stage, is interposed between successive ones of said plurality of impactor stages, while at the same time, each one of said plurality of impactor plates is interposed between an upper one and a lower one of said pairs of isolation stages, and each one of said impactor stages is interposed between a lower isolation stage of an upper pair of said plurality of isolation stages and an upper isolation stage of a successively lower pair of said plurality of isolation stages.

3. The automated cascade impactor as set forth in claim 1, further comprising:

an extension actuator operatively connected to at least one of said plurality of impactor stages so as to permit all of said plurality of impactor stages to move vertically away from each other such that all of said plurality of impactor stages are disposed in separated states with respect to each other, and to cause said plurality of impactor stages to move vertically toward each other such that all of said plurality of impactor stages are disposed in compressed states with respect to each other;

an isolation actuator operatively connected to all of said plurality of isolation stages so as to respectively insert all of said plurality of isolation stages into spaces respectively defined between all of said plurality of impactor stages, and to respectively remove all of said plurality of isolation stages out from said spaces respectively defined between all of said plurality of impactor stages, when all of said plurality of impactor stages are disposed in said separated states with respect to each other, and to be respectively compressed between all of said plurality of impactor stages when all of said plurality of impactor stages are disposed in said compressed states with respect to each other whereby all of said plurality of isolation stages can isolate all of said plurality of impactor stages from each other.

4. The automated cascade impactor as set forth in claim 2, wherein:

said gripper arm assembly comprises an upstanding standard;

a plurality of gripper arms are fixedly mounted upon said upstanding standard in vertically spaced pairs of gripper arms wherein each pair of gripping arms can grip one of said impactor plates when transferring said impactor plates from said impactor stages to said isolation stages, and when transferring said impactor plates from said isolation stages back to said impactor stages.

5. The automated cascade impactor as set forth in claim 4, wherein:

dependent gripper arm pins depend from distal end portions of said gripper arms for gripping external peripheral portions of said impactor plates.

6. The automated cascade impactor as set forth in claim 5, wherein:

said gripper arm assembly comprises structure for enabling movement of said gripper arms with multiple degrees of freedom whereby said plurality of pairs of gripper arms are able to be moved toward and away from said impactor stages, said plurality of gripper arms are able to be elevationally moved upwardly and downwardly so as to be disposed at elevational levels at which said plurality of gripper arms can remove said impactor plates from said impactor stages and deposit said impactor plates within said isolation stages, and said plurality of gripper arms are able to be moved toward and away from each other such that said pairs of gripper arm pins can grip and release said impactor plates.

7. The automated cascade impactor as set forth in claim 6, wherein said structure for enabling said movement of said gripper arms with multiple degrees of freedom comprises:

a first linear guide rail and slide block for enabling said gripper arms to be moved toward and away from said impactor stages, a second guide rail and second slide blocks for moving said plurality of gripper arms toward and away from each other, and a rack and pinion drive for moving said plurality of gripper arms elevationally upwardly and downwardly.

8. The automated cascade impactor as set forth in claim 5, further comprising:

an impactor plate gripper arm pin wash assembly for washing and cleaning said gripper arm pins such that cross-contamination does not occur between drug doses.

9. The automated cascade impactor as set forth in claim 8, wherein said impactor plate gripper arm pin wash assembly comprises:

an upstanding standard;

a plurality of vertically spaced washer plates fixedly mounted upon said upstanding standard; and a pair of impactor plate gripper arm pin wash wells formed upon each one of said plurality of vertically spaced washer plates for receiving said gripper arm pins dependent from distal end portions of said gripper arms.

10. The automated cascade impactor as set forth in claim 1, wherein:

said plurality of impactor stages and said plurality of isolation stages are mounted upon a framework;

a rotary drive motor, having a rotary output drive shaft, for imparting rotational movements to said framework, said plurality of impactor stages, and said plurality of isolation stages; and a mounting bracket fixedly mounted upon a distal end portion of said rotary output drive shaft of said rotary drive motor for mounting said framework, said plurality of impactor stages, and said plurality of isolation stages upon said rotary drive motor.

11. The automated cascade impactor as set forth in claim 10, wherein:

said rotary drive motor is mounted upon linear guide rails such that linear reciprocation movements can also be imparted to said framework, said plurality of impactor stages, and said plurality of isolation stages.

12. The automated cascade impactor as set forth in claim 10, wherein:

auxiliary vibrators are mounted upon said plurality of isolation stages so as to impart additional vibrations to said plurality of isolation stages.

13. The automated cascade impactor as set forth in claim 1, wherein:

each one of said upper and lower isolation stages of a pair of said plurality of isolation stages is provided with a pair of diametrically opposed solvent ports for injecting and extracting solvent into and out from said upper and lower isolation stages.

14. The automated cascade impactor as set forth in claim 2, wherein:

each one of said upper isolation stages of each pair of said plurality of isolation stages is provided with a pair of diametrically opposed solvent ports for injecting and extracting solvent into and out from said centrally recessed portion defined within said upper isolation stage for receiving one of said impactor plates from one of said plurality of impactor stages.

15. The automated cascade impactor as set forth in claim 2, wherein:

each one of said lower isolation stages of each pair of said plurality of isolation stages is provided with a pair of diametrically opposed solvent ports for injecting and extracting solvent into and out from a centrally recessed portion defined within said lower isolation stage for receiving an upper peripheral portion of one of said plurality of impactor stages.

16. The automated cascade impactor as set forth in claim 2, wherein:

said lower isolation stage of a first pair of said plurality of isolation stages is provided with an air/vacuum port, while said upper isolation stage of a second pair of said plurality of isolation stages is also provided with an air/vacuum port, wherein one of said impactor stages is interposed between said lower isolation stage of said first pair of said plurality of isolation stages and said upper isolation stage of said second pair of said plurality of isolation stages, whereby a pressure differential can be created across said impactor stage interposed between said lower isolation stage of said first pair of said plurality of isolation stages and said upper isolation stage of said second pair of said plurality of isolation stages such that solvent can be caused to traverse said impactor stage interposed between said lower isolation stage of said first pair of said plurality of isolation stages and said upper isolation stage of said second pair of said plurality of isolation stages.

17. The automated cascade impactor as set forth in claim 2, wherein:

frits/membranes are disposed adjacent to said air/vacuum ports defined within said lower isolation stage of said first pair of said plurality of isolation stages and within said upper isolation stage of said second pair of said plurality of isolation stages so as to permit only air and vacuum conditions to pass through said air/vacuum ports defined within said lower isolation stage of said first pair of said plurality of isolation stages and within said upper isolation stage of said second pair of said plurality of isolation stages.

18. The automated cascade impactor as set forth in claim 3, wherein:

said movements of said extension actuator and said isolation actuator are controlled by a programmable logic computer (PLC).

* * * * *